US010725452B2

(12) United States Patent
Elber et al.

(10) Patent No.: US 10,725,452 B2
(45) Date of Patent: Jul. 28, 2020

(54) SYSTEMS AND METHODS FOR MANUFACTURING OF MICROSTRUCTURES

(71) Applicant: Technion Research & Development Foundation Limited, Haifa (IL)

(72) Inventors: Gershon Elber, Haifa (IL); Fady Massarwi, Baka al Gharbiya (IL); Jinesh Machchhar, Nesher (IL)

(73) Assignee: Technion Research & Development Foundation Limited, Haifa (IL)

( * ) Notice: Subject to any disclaimer, the term of this patent is extended or adjusted under 35 U.S.C. 154(b) by 2 days.

(21) Appl. No.: 15/985,846

(22) Filed: May 22, 2018

(65) Prior Publication Data

US 2018/0275637 A1  Sep. 27, 2018

Related U.S. Application Data

(63) Continuation-in-part of application No. 15/919,705, filed on Mar. 13, 2018.

(Continued)

(51) Int. Cl.
*G05B 19/4099* (2006.01)
*G06T 11/20* (2006.01)
*G06T 17/10* (2006.01)
*B33Y 50/02* (2015.01)
*G06T 19/20* (2011.01)

(Continued)

(52) U.S. Cl.
CPC .......... *G05B 19/4099* (2013.01); *B33Y 50/02* (2014.12); *G06T 11/206* (2013.01); *G06T 17/10* (2013.01); *G06T 19/20* (2013.01); *A61B 34/10* (2016.02); *A61F 2002/30943* (2013.01); *G05B 19/418* (2013.01); *G05B 2219/35134* (2013.01); *G05B 2219/35499* (2013.01); *G05B 2219/49007* (2013.01); *G06T 2219/2021* (2013.01)

(58) Field of Classification Search
None
See application file for complete search history.

(56) References Cited

U.S. PATENT DOCUMENTS 6,313,837 B1 * 11/2001 Assa ............... G06T 17/20
345/420
7,996,101 B2 * 8/2011 Menchik ............... B41J 2/175
700/119

(Continued)

OTHER PUBLICATIONS

Official Action dated May 24, 2019 From the US Patent and Trademark Office Re. U.S. Appl. No. 15/919,705. (31 Pages).

(Continued)

*Primary Examiner* — Ramesh B Patel

(57) ABSTRACT

There is provided a method of generating instructions for manufacturing a microstructure by a manufacturing device, comprising: providing a representation of a freeform tile, providing a representation of a deformation map that maps a parameter space to a space of an object, arranging a plurality of instances of the freeform tile within at least a portion of a domain of the deformation map to create a tile arrangement, creating a representation a microstructure of the object by composing the tile arrangement into the deformation map, and providing code instructions for execution by a manufacturing device controller of a manufacturing device for manufacturing the microstructure.

20 Claims, 22 Drawing Sheets

Related U.S. Application Data

(60) Provisional application No. 62/470,399, filed on Mar. 13, 2017.

(51) Int. Cl.
    *G05B 19/418*     (2006.01)
    *A61B 34/10*     (2016.01)
    *A61F 2/30*     (2006.01)

(56) References Cited

U.S. PATENT DOCUMENTS

| | | | | |
|---|---|---|---|---|
| 9,972,128 | B2 * | 5/2018 | Gregson | G06T 17/20 |
| 10,108,752 | B2 * | 10/2018 | Maisonneuve | G06T 17/20 |
| 10,366,535 | B2 * | 7/2019 | Huang | G06T 17/005 |
| 2006/0290695 | A1 * | 12/2006 | Salomie | G06T 17/20 |
| | | | | 345/420 |
| 2015/0038860 | A1 * | 2/2015 | Fonte | A61B 6/50 |
| | | | | 600/505 |
| 2015/0298423 | A1 * | 10/2015 | Holemans | B32B 5/18 |
| | | | | 244/133 |
| 2016/0224693 | A1 * | 8/2016 | Maisonneuve | G06T 17/20 |
| 2017/0116779 | A1 * | 4/2017 | Lalish | G06T 15/04 |
| 2018/0373816 | A1 * | 12/2018 | Maisonneuve | G06T 17/20 |

OTHER PUBLICATIONS

Li et al. "Interactive Volume Illustration Using Wang Cubes", ECE Technical Reports, pp. 1-39, Oct. 2004.

Official Action dated Sep. 23, 2019 From the US Patent and Trademark Office Re. U.S. Appl. No. 15/919,705. (35 pages).

Official Action dated Feb. 12, 2020 From the US Patent and Trademark Office Re. U.S. Appl. No. 15/919,705. (39 pages).

Advisory Action Before the Filing of an Appeal Brief dated Dec. 13, 2019 From the US Patent and Trademark Office Re. U.S. Appl. No. 15/919,705. (4 pages).

DeRose et al. "Functional Composition Algorithms Via Blossoming", ACM Transactions on Graphics, TOG, 12(2): 113-135, Apr. 1, 1993.

\* cited by examiner

Pseudo code

TopoSubdiv: Topological subdivision of $\mathcal{D}$'s domain

Input:
$\mathcal{D}$: a deformation map;
$D$: sub-domain of $\mathcal{D}$ to subdivide;
$\epsilon$: a subdivision threshold;
Output: a topological tiling of the domain of $\mathcal{D}$;
Algorithm:
1: $\mathcal{E}$ := twelve edges of $D$'s box;
2: $e_{max}$ := edge in $\mathcal{E}$ with maximal length under $\mathcal{D}$'s image;
3: if $\|e_{max}\| < \epsilon$ then
4:     return $D$;
5: end if
6: $axis_e$ := parametric direction of $e_{max}$;
7: $\{D_L, D_R\}$ := Subdivide $D$ in the middle, along $axis_e$;
8: return TopoSubdiv($\mathcal{D}, D_L, \epsilon$) $\cup$ TopoSubdiv($\mathcal{D}, D_R, \epsilon$);

FIG. 5

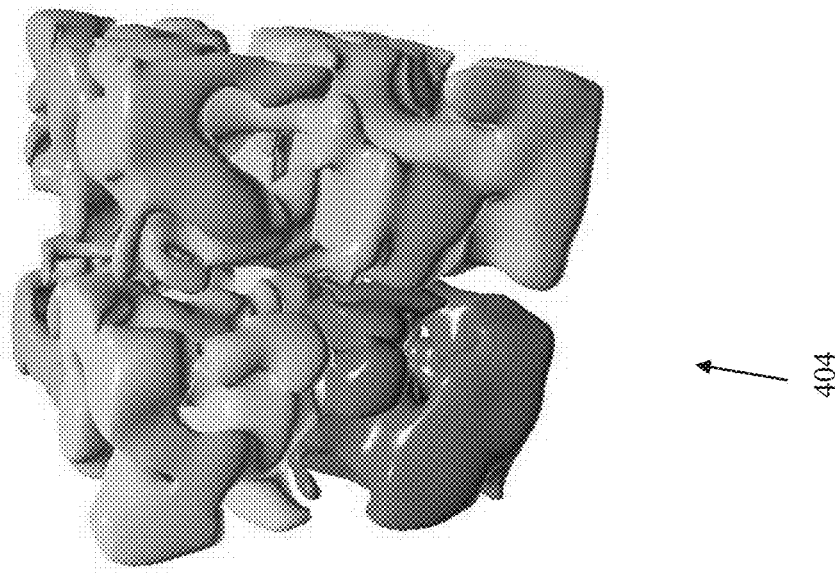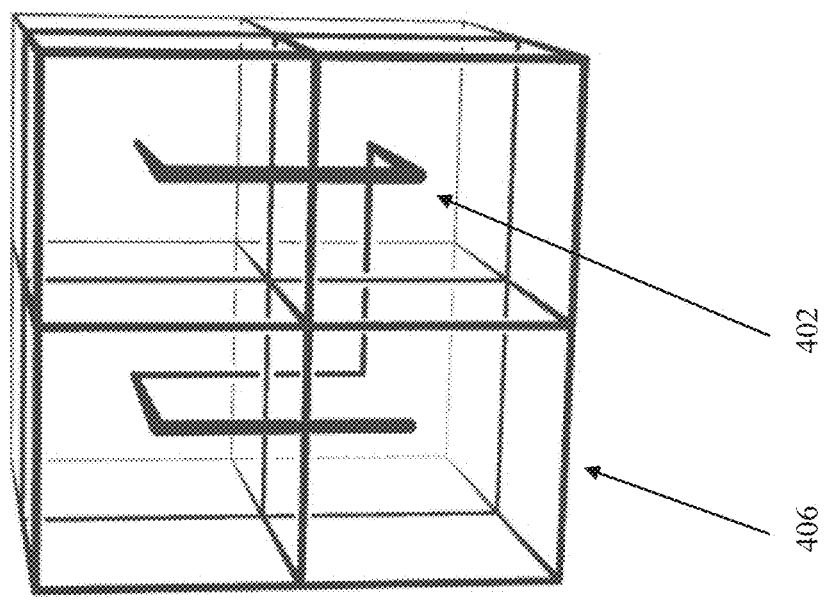
FIG. 10

SYSTEMS AND METHODS FOR MANUFACTURING OF MICROSTRUCTURES

RELATED APPLICATIONS

This application is a Continuation-In-Part (CIP) of U.S. Utility application Ser. No. 15/919,705 filed on Mar. 13, 2018, which claims the benefit of priority under 35 USC § 119(e) of U.S. Provisional Patent Application No. 62/470,399 filed on Mar. 13, 2017. The contents of the above applications are all incorporated by reference as if fully set forth herein in their entirety.

FIELD AND BACKGROUND OF THE INVENTION

The present invention, in some embodiments thereof, relates to microstructures and, more specifically, but not exclusively, to systems and methods for manufacturing a microstructure.

Advances in additive manufacturing have enabled fabrication of a range of artifacts with complex and interesting properties. Use of composites, comprising of several materials, has grown rapidly. Microstructures are implemented in a wide range of applications, for example, aviation, and designing scaffold structures in tissue engineering, for example, as described with reference to Armillotta, A., Pelzer, R., November 2008. *Modeling of porous structures for rapid prototyping of tissue engineering scaffolds. The International Journal of Advanced Manufacturing Technology* 39 (5), 501-511.

The computer aided design approach towards the creation of micro-structures is a relatively nascent area, mostly due to the difficulty in manufacturing such shapes. Recent advances in additive manufacturing have opened new avenues in this direction, for example, as described with reference to Gao, W, Zhang, Y., Ramanujan, D., Ramani, K., Chen, Y, Williams, C. B., Wang, C. C., Shin, E C., Zhang, S., Zavattieri, P. D., 2015. *The status, challenges, and future of additive manufacturing in engineering. Computer-Aided Design* 69 (Supplement C), 65-89.

SUMMARY OF THE INVENTION

According to a first aspect, a method of generating instructions for manufacturing a microstructure by a manufacturing device, comprises: providing a representation of a freeform tile, providing a representation of a deformation map that maps a parameter space to a space of an object, arranging a plurality of instances of the freeform tile within at least a portion of a domain of the deformation map to create a tile arrangement, creating a representation a microstructure of the object by composing the tile arrangement into the deformation map, and providing code instructions for execution by a manufacturing device controller of a manufacturing device for manufacturing the microstructure.

According to a second aspect, system for computing a model of a microstructure of a three dimensional (3D) object, comprises: a non-transitory memory having stored thereon a code for execution by at least one hardware processor, the code comprising: code for designating a representation of a freeform(s) tile, code for designating a representation of a deformation map that maps a parameter space to a 3D space of an object, code for arranging a plurality of instances of the tile within at least a portion of a domain of the deformation map to create a tile arrangement, code for creating a representation of a microstructure of the object by composing the tile arrangement into the deformation map.

According to a third aspect, a method of computing a model of a microstructure, comprises: providing a representation of a freeform tile, providing a representation of a deformation map that maps a parameter space to a space of an object, arranging a plurality of instances of the freeform tile within at least a portion of a domain of the deformation map to create a tile arrangement, creating a representation a microstructure of the object by composing the tile arrangement into the deformation map, and providing the representation of the microstructure.

At least some of the systems, apparatus, methods, and/or code instructions (i.e., stored in a data storage device executable by hardware processor(s)) described here relate to the technical problem of manufacturing microstructures, optionally by an additive manufacturing device (e.g., 3D printer).

At least some of the systems, apparatus, methods, and/or code instructions (i.e., stored in a data storage device executable by hardware processor(s)) described here relate to the technical problem of creating models of microstructure for analysis, simulation, and/or evaluation.

At least some of the systems, methods, apparatus, and/or code instructions described herein relate to an improved process for generating models of microstructures for analysis, simulation, and/or evaluation. For example, the improved models of the microstructures may be used to simulate, analyze, evaluate and/or improve: rigidity, stability, high strength to weight, a hierarchical structure, uniformly sized tiles, precise complex shapes, and/or smooth and/or continuous surfaces.

At least some of the systems, methods, apparatus, and/or code instructions described herein relate to an improved process for manufacturing microstructures, optionally by an additive manufacturing device and/or other manufacturing devices described herein. For example, the improved manufactured microstructures have an improved optimized internal structure of the material, for example, improved rigidity, stability, high strength to weight ratio, a hierarchical structure, uniformly sized tiles, precise complex shapes, and/or smooth and/or continuous surfaces. For example, the created microstructure of the object is porous, resulting in relatively low weight in comparison to a non-porous object, while having high strength.

In a further implementation form of the first, second, and third aspects, a single branch-in surface and one or more branch-out surfaces are defined for the tile, wherein the tile arrangement is created by iteratively mapping the respective single branch-in surface of each of the tiles at a next level to a respective branch-out surface of each tile at a current level.

In a further implementation form of the first, second, and third aspects, the single branch-in surface is larger than each of the one or more branch-out surfaces, wherein a volume of each of the tiles of the tile arrangement at the next level is adjusted such that the respective single branch-in surface of each of the tiles at the next level is continuous with the respective branch-out surface of each tile at the current level.

In a further implementation form of the first, second, and third aspects, the iterations for arranging the tiles is performed for a predefined number of tile levels for filing at least the portion of the domain of the deformation map.

In a further implementation form of the first, second, and third aspects, the one or more branch-out surfaces are based on a geometric bifurcation of the tile created by a partial Euclidean discontinuity.

In a further implementation form of the first, second, and third aspects, the single branch-in surface and each of the one or more branch-out surfaces are designated according to a plurality of boundary surfaces of the tile.

In a further implementation form of the first, second, and third aspects, the method and/or the system further comprise reducing the degree of the representation of the microstructure by approximating freeforms of the representation of the microstructures as lower order degrees.

In a further implementation form of the first, second, and third aspects, the method and/or the system further comprise providing a plurality of different freeform(s) tiles, wherein the tile arrangement is created by arranging the plurality of different tiles within the domain of the deformation map, and further comprising computing a single globally connected component of the tile arrangement by ensuring a topological connectivity between all of the tiles of the tile arrangement.

In a further implementation form of the first, second, and third aspects, the topological connectivity is ensured by: computing a graph having vertices according to centers of each tile of the tile arrangement, and edges of the graph are according to connections between neighboring tiles that have connecting faces, computing a first spanning tree according to edges of the graph that connects the tiles of the tile arrangement, wherein all of the tiles of the tile arrangements are connected into a single global component when the first spanning tree includes all of the tiles of the tile arrangement.

In a further implementation form of the first, second, and third aspects, the method and/or the system further comprise removing the edges included in the first spanning tree from the graph to create a second graph, computing a second spanning tree according to the second graph, and adjusting at least one of the tiles of the tile arrangement to connect the first graph and the second graph for creating the single global component.

In a further implementation form of the first, second, and third aspects, each of the tiles of the tile arrangement is randomly generated, wherein each of the randomly generated tiles is created within a respective cell of a grid of the domain of the deformation map, wherein the tiles are randomly generated according to similar control coefficients along common boundaries of respective cells of the grid to create continuity between adjacent randomly generated tiles.

In a further implementation form of the first, second, and third aspects, the method and/or the system further comprise creating a non-grid topology by subdividing the domain of the deformation map into a plurality of cells, wherein each of the tiles of the tile arrangement located in a respective cell of the plurality of cells is mapped by a respective subdivision of the domain of the deformation map to a same size in object space within a tolerance requirement.

In a further implementation form of the first, second, and third aspects, at least one of the tiles of the tile arrangement includes an automatically created bifurcated tile computed according to bifurcation cells created by the subdivision of the domain of the deformation map.

In a further implementation form of the first, second, and third aspects, domain of the deformation map is divided to include bifurcation cells according to bifurcation tiles of the tile arrangement.

In a further implementation form of the first, second, and third aspects, the method and/or the system further comprise sealing the tile arrangement along the boundaries of the deformation map.

In a further implementation form of the first, second, and third aspects, sealing comprises capping open holes of the tile arrangement of the tile along boundaries of the deformation map.

In a further implementation form of the first, second, and third aspects, sealing comprises creating a shell having a predefined thickness that encompasses the tile arrangement along boundaries of the deformation map.

In a further implementation form of the first, second, and third aspects, at least one surface of each of the plurality of instances of the freeform tile coincides and is connected with at least one other surface of another of at least one of the plurality of instances of the freeform tile creating smooth continuity between the tiles of the tile arrangement.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 5 includes pseudo code of a process of performing topological subdivision of a domain of a deformation map, in accordance with some embodiments of the present invention;

FIG. 10 is a schematic depicting an example of a first spanning tree (L1) computed for a tile structure, in accordance with some embodiments of the present invention;

DESCRIPTION OF SPECIFIC EMBODIMENTS OF THE INVENTION

Figure 1A:
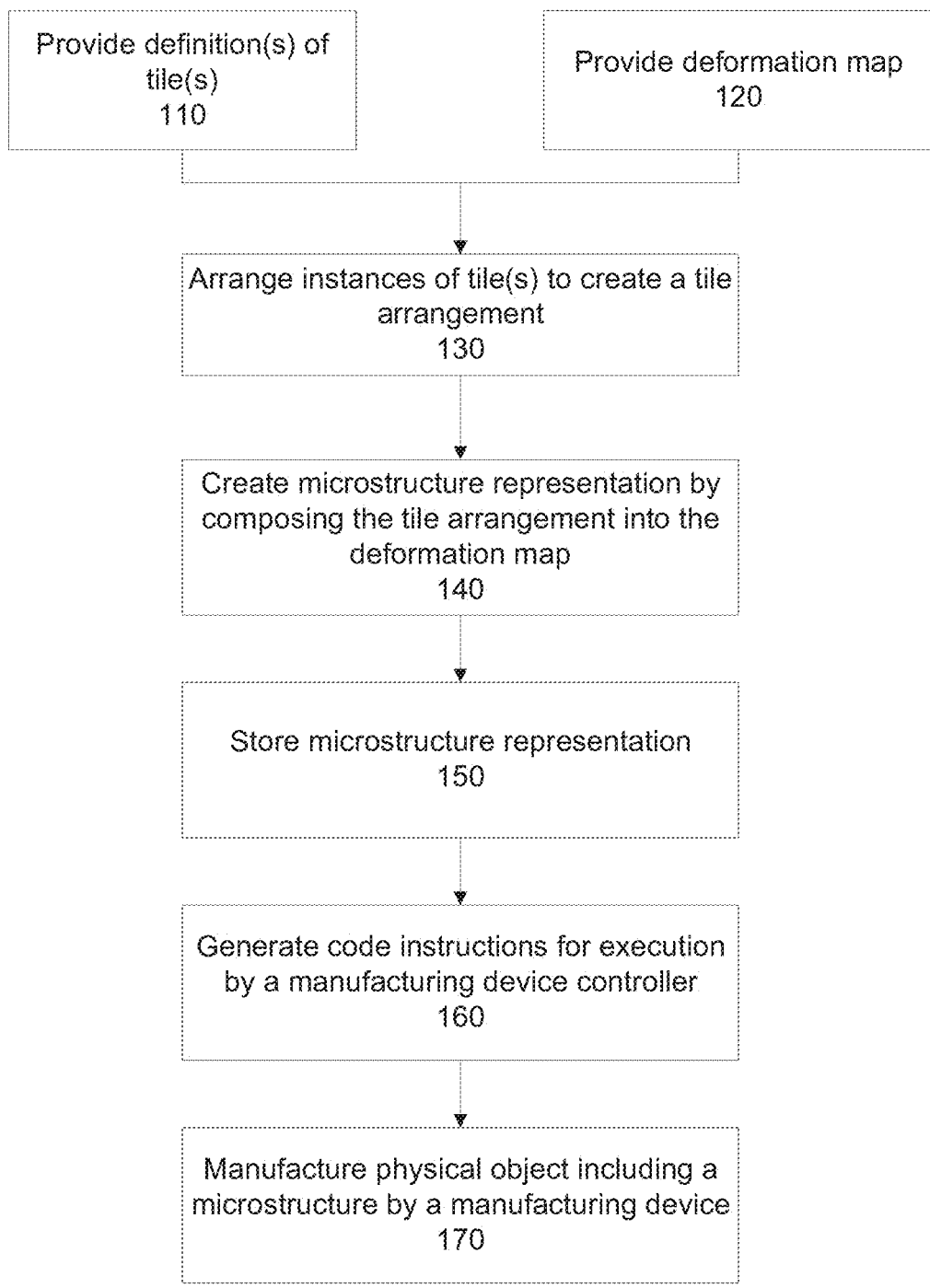
FIG. 1A is a flowchart of a method for manufacturing a microstructure of a 3D object based on an arrangement of instances of a tile(s), in accordance with some embodiments of the present invention.

The present invention, in some embodiments thereof, relates to microstructures and, more specifically, but not exclusively, to systems and methods for manufacturing a microstructure.

An aspect of some embodiments of the present invention relates to systems, methods, apparatus, and/or code instructions (i.e., stored in a data storage device, executable by one or more hardware processors) for generating instructions for manufacturing a microstructure of a three dimensional (3D) object, optionally by an additive manufacturing device. A representation(s) of one or more tiles (e.g., The tile may be implicit and/or parametric, univariates, bivariates, trivariates, optionally trimmed, or any combination thereof (referred to as freeform(s) herein)) are arranged within a domain of a deformation map (e.g., a bivariate or a trivariate deformation map or higher dimension).

It is noted that the implementation described herein of trivariate deformation maps in $R^3$ serves as a non-limiting example) to create a tile arrangement. The deformation map maps a parameter space to a 3D space of the object. The freeform(s) of each of the tiles of the tile arrangement coincide and are connected with one or more other freeform(s) of other tiles of the tile arrangement, creating smooth continuity between the tiles of the tile arrangement, depending on the continuity of the tile and the deformation map. The representation of the microstructure of the object is created by composing the tile arrangement into the trivariate deformation map.

A tangible microstructure may be manufactured based on the computed representation. Code instructions may be generated for execution by a manufacturing device controller for manufacturing the microstructure. The microstructure may be manufactured, for example, in 2D (e.g., as a manifold, and/or a 2D structure on a surface), in 3D, and/or in 4D. Examples of manufacturing devices include: an additive manufacturing device for additive manufacturing of the microstructure, a 3D printer for 3D printing of the microstructure, a bioprinter for bioprinting of the microstructure, a fabrication machine for fabrication of the microstructure, a manufacturing device that manufactures parts for assembly by another device and/or parts that self assembly. The manufacturing device may implement different manufacturing methods, for example, based on a scallop, and/or template, and/or any combination of the aforementioned.

The representation of the microstructure may be further processed, without necessarily being manufactured. For example, the microstructure may be generated to model structures, for example, bones. Modeling may be performed to simulate and/or analyze (e.g., compute rigidity and/or stability of) the microstructures, optionally in response to external forces (e.g., effect of body mass on bone stability). The microstructure may be adjusted according to the simulation and/or analysis, for example, to increase rigidity and/or stability. The modeled and/or simulated and/or analyzed microstructure may or may not be manufactured.

Optionally, a single branch-in surface and (at least one) branch-out surface(s) are defined for the tile. The tile arrangement is created by iteratively mapping the respective single branch-in surface of each of the tiles at a next level to a respective branch-out surface of each trivariate tile at a current level.

Optionally, the degree of the representation of the microstructure is reduced by approximating curves/surfaces/trivariates of the representation of the microstructures as quadratic degree(s) and/or cubic degree(s). End/corner points of approximated freeform(s) are interpolated. Tangents at end/corner points of cubic degree approximated freeform(s) are reconstructed.

Optionally, multiple different tiles are utilized in the tile arrangement, for example, randomly created tiles. A single globally connected component of the tile arrangement is computed by ensuring a topological surface connectivity between all of the tiles of the tile arrangement.

Optionally, a non-grid topology is created by subdividing the domain of the deformation map into multiple cells, optionally including bifurcation cells. Bifurcation tiles are arranged within corresponding bifurcation cells. The tiles of the tile arrangement located in respective cells are mapped by respective subdivisions of the domain of the trivariate deformation map to approximately the same size in object (e.g., Euclidean) space, for example, where the same size is defined according to a tolerance requirement.

Optionally, the tile arrangement is sealed along boundary surfaces of the trivariate deformation map. Sealing may be performed by capping holes of the tile arrangement and/or creating a shell around the tile arrangement.

At least some of the systems, apparatus, methods, and/or code instructions (i.e., stored in a data storage device executable by hardware processor(s)) described here relate to the technical problem of manufacturing microstructures, optionally by an additive manufacturing device (e.g., 3D printer).

At least some of the systems, apparatus, methods, and/or code instructions (i.e., stored in a data storage device executable by hardware processor(s)) described here relate to the technical problem of creating models of microstructure for analysis, simulation, and/or evaluation.

At least some of the systems, methods, apparatus, and/or code instructions described herein relate to an improved process for generating models of microstructures for analysis, simulation, and/or evaluation. For example, the improved models of the microstructures may be used to simulate, analyze, evaluate and/or improve: rigidity, stability, high strength to weight, a hierarchical structure, uniformly sized tiles, precise complex shapes, and/or smooth and/or continuous surfaces.

At least some of the systems, methods, apparatus, and/or code instructions described herein relate to an improved process for manufacturing microstructures, optionally by an additive manufacturing device and/or other manufacturing devices described herein.

For example, the improved manufactured microstructures have an improved optimized internal structure of the material, for example, improved rigidity, stability, high strength to weight ratio, a hierarchical structure, uniformly sized tiles, precise complex shapes, and/or smooth and/or continuous surfaces. For example, the created microstructure of the object is porous, resulting in relatively low weight in comparison to a non-porous object, while having high strength.

The improved microstructures are manufactured according to a model created by arranging instances of a tile within a domain of a deformation map, and composing the tile arrangement with the deformation map. The model is created based on a unique process.

The improved process for manufacturing microstructures may be implemented, for example, in aviation to create lighter and/or stronger structures (e.g., airplanes, helicopters, drones), to manufacture scaffold structures used in tissue engineering application, and manufacture heat sinks where the goal is to maximize the dissipation of heat while minimizing the volume of the material used. Heat sinks are discussed in additional detail, for example with reference to Bornoff, R., Parry, J., March 2015. *An additive design heatsink geometry topology identification and optimisation algorithm. In:* 2015 31*st Thermal Measurement, Modeling Management Symposium* (*SEMI-THERM*). pp. 303-308.

When the features related to by the systems, methods, apparatus, and/or code instructions described herein are taken as a whole, the combination of the features amounts to significantly more than a simple mathematical calculation of a geometric model of a microstructure. The systems, methods, apparatus, and/or code instructions described herein do not merely relate to mathematical computations, but relate to the particular way in which tiles are arranged and the particular way in which the model of the microstructure is created by a deformation map that maps the arranged tiles into the microstructure.

At least some of the systems, methods, apparatus, and/or code instructions described herein improve an underling technical process within the technical field of manufacturing microstructures.

Accordingly, the systems and/or methods described herein are inextricably tied to computer technology and manufacturing technology, optionally additive manufacturing technology (e.g., 3D printing technology) to overcome an actual technical problem arising in manufacturing of geometric objects.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages.

The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures.

For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, the term additive manufacturing, and/or 3D printing are not necessarily limiting examples of types of manufacturing for creating a tangible object according to the representation of the microstructure. Other types of manufacturing methods and/or manufacturing devices may sometimes be substituted.

As used herein, the 3D representation of the tile and/or the 3D representation of the deformation map represent an exemplary implementation, and are not necessarily limiting. For example, the tile and/or deformation map may be defined in any dimension and/or having an arbitrary number of dimensions. Therefore, the term 3D tile and/or 3D deformation map and/or trivariate are exemplary, not necessarily limiting, and may sometimes be substituted with lower or higher number of dimensions.

As used herein, the terms model and representation may sometimes be interchanged.

As used herein, the terms surface and face (i.e., of a tile) may be interchanged.

At least some of the systems, methods, apparatus, and/or code instructions described herein provide technical solutions to technical problems that are not solved by other systems and/or methods, and/or provide an improvement to the technology of manufacturing microstructures, for example, improved technical solutions to the technical problems addressed by other systems and/or methods. For example, at least some of the systems, methods, apparatus, and/or code instructions described herein provide the following features that improve manufacturing of microstructures, which are not addressed by other systems and or methods: support for freeform parametric geometry providing for precise additive manufacturing of complex shapes, a high degree of numerical precision leading to additive manufacturing of water-tight structures, support for bifurcations in the tiles providing for additive manufacturing of hierarchical structures and/or fractal like structures, compensation for the non-isometric behavior of the deformation map which provides for additive manufacturing of microstructures having substantially uniform tile shapes (i.e., when otherwise different instances of the same tile would have vastly different sizes), support for heterogeneous materials which provides for additive manufacturing of microstructures having local heterogeneity resulting from definitions of materials by the tile which are locally adapted by the deformation map, support for additive manufacturing of hierarchical structures which have a high surface to volume ratio useful in applications for example such as heat sinks, and additive manufacturing of microstructures having a high degree of precision even when functions representing the microstructures are approximated by polynomial degree reduction. Some examples of previous method are now described, the shortcomings of which are addressed by at least some of the systems, methods, apparatus, and/or code instructions described herein.

For example, Burczynski, T., Ku's, W., 2009. *Microstructure Optimization and Identification in Multi-scale Modelling*. Springer Netherlands, Dordrecht, pp. 169-181 appear to perform optimization of microstructures towards multi-scale modeling. A set of parameters is identified at the microscale which govern properties such as the shape, stress, strain, and other properties of the model. The finite element method is used for the analysis step. Evolutionary schemes, which are based on genetic algorithms, are used to search for optimal values of parameters. The NURBS representation is used for the shape of the structures. This previous method lacks precision, which is addressed by at least some of the systems, methods, apparatus, and/or code instructions described herein.

In another example, Conde-Rodriguez, F., Torres, J.-C., Garcia-Fernandez, A'-L., Feito-Higueruela, F.-R., January 2017. *A comprehensive framework for modeling heterogeneous objects. The Visual Computer* 33 (1), 17-31 appears to present a framework for modeling heterogeneous objects using trivariate Bézier patches. The Bézier patches have two sets of coordinates. The first set of three coordinates, (x, y, z), prescribe the shape of the object, while the rest of the coordinates specify the material composition of the object. This method admits a single level of details, and is limited to Bézier trivariates only. This previous method cannot model micro-structures.

In another example, Schroeder, C., Regli, W. C., Shokoufandeh, A., Sun, W., 2005. *Computeraided design of porous artifacts. Computer-Aided Design* 37 (3), 339-353, *heterogeneous Object Models and their Applications* appears to adopt principles from stochastic geometry for designing porous artifacts, for example, as described with reference to Kendall, W. S., van Lieshout, M., 1998. *Stochastic Geometry: Likelihood and Computation*. Chapman and Hall/CRC, London. This previous method is unsuitable for applications requiring a high degree of precision, for example, designing a wing of an aircraft. Moreover, this method doesn't address connectivity of the porous structures, which is addressed by at least some of the systems, methods, apparatus, and/or code instructions described herein.

In yet another example, Xiao, F., Yin, X., 2016. *Geometry models of porous media based on voronoi tessellations and their porosity-permeability relations. Computers and Mathematics with Applications* 72 (2), 328-348, *the Proceedings of ICMMES* 2014 appears to use Voronoi tessellations to generate random porous structures of three kinds: porous geometries with intersecting fractures, interconnected tubes and fibers. A set of points is randomly sampled in the space which gives rise to Voronoi tessellations. Offsets are then computed for the edges of the tessellations to generate the three kinds of microstructures. This method is limited to constructing geometry which is piecewise linear or cylindrical.

In yet another example, Pasko, A., Fryazinov, O., Vilbrandt, T., Fayolle, P.-A., Adzhiev, V., 2011. *Procedural function-based modelling of volumetric microstructures. Graphical Models* 73 (5), 165-181, appears to use implicit surfaces for modeling microstructures. This method does not readily support creation of heterogeneous media. Moreover, the extension to parametric representation is not directly supported. Additionally, this method doesn't guarantee connectivity for the case of irregular (e.g., random) structures.

In yet another example, Armillotta, A., Pelzer, R., November 2008. *Modeling of porous structures for rapid prototyping of tissue engineering scaffolds. The International Journal of Advanced Manufacturing Technology* 39 (5), 501-511, appears to relate to creating scaffolds as support structures for tissue engineering. The scaffolds, once fabricated out of some biodegradable or bioresorbable material, are seeded with (biological) cells and provide support and shape to tissue during its growth. The scaffolds are modeled as porous micro-structures using polygonal representation. This method does not generalize to freeform spline geometry and heterogeneous materials are not supported, which are addressed by at least some of the systems, methods, apparatus, and/or code instructions described herein.

In yet another example, Wang, H., Chen, Y., Rosen, D., January 2005. *A hybrid geometric modeling method for large scale conformal cellular structures. In: Volume* 3: *25th Computers and Information in Engineering Conference, Parts A and B.*, appears to relate to a method for designing mesoscopic structures using trusses. The output is in the form of triangles in STL format. Since this method is tailored to trusses as the basic building blocks of the structure, it has limited scope of application.

In yet another example, Chu, C., Graf G., Rosen, D. W., 2008. *Design for additive manufacturing of cellular structures. Computer-Aided Design and Applications* 5 (5), 686-696 appears to relate to a framework for designing additive manufacturing of mesostructures. This method is based upon the process-structure-property-behavior model. The basic building element is an octet truss which is represented parametrically. Extension for support of other types of elements is lacking.

In yet another example, Medeiros e Sa, A., Mello, V. M., Rodriguez Echavarria, K., Covill, D., June 2015. *Adaptive voids. The Visual Computer* 31 (6), 799-808, appears to relate to a method for designing cellular structures geared towards additive manufacturing. The cellular structure is achieved through an adaptive triangulation of the interior of the solid, with finer tetrahedra along the boundary of the solid. This method appears to supports a dual construction obtained from the Voronoi diagram of the triangulation. This method does not generalize to freeform geometry.

Figure 1B:
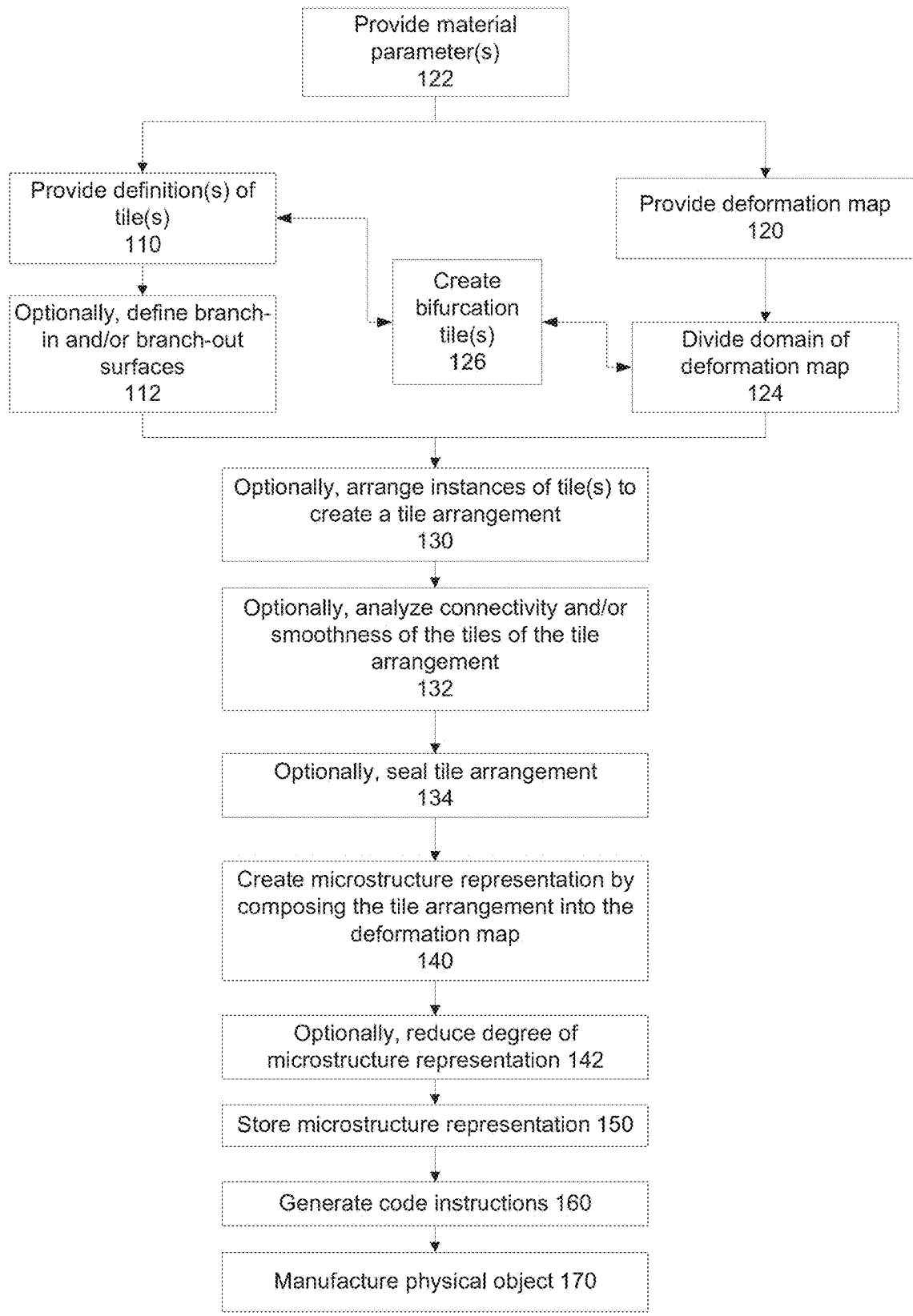
FIG. 1B is a flowchart of one or more additional features for manufacturing a microstructure of a 3D object based on at least one definition of a tile and a deformation map, in accordance with some embodiments of the present invention.
Figure 2:
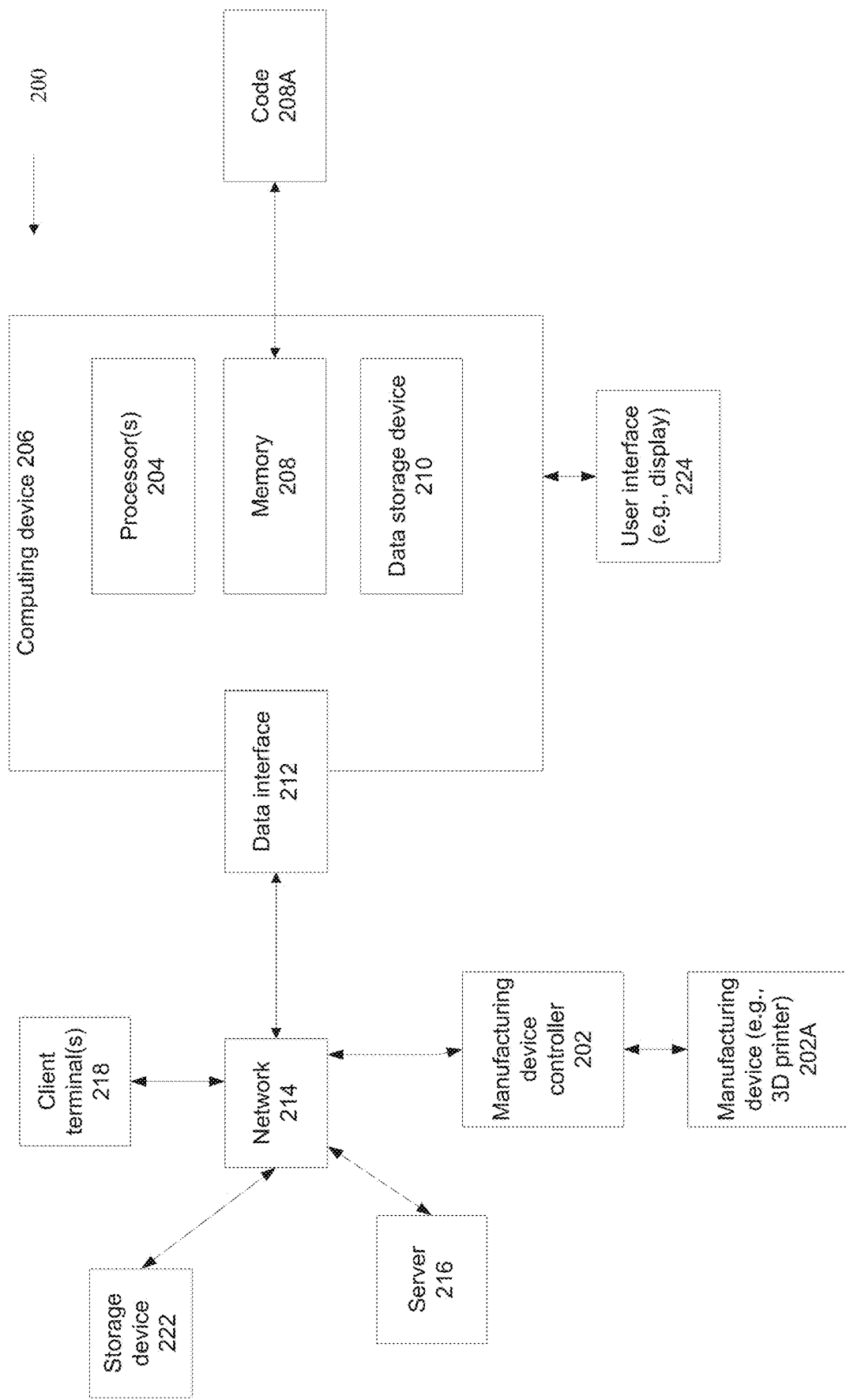
FIG. 2 is a block diagram of a system for manufacturing a microstructure of a 3D object based on an arrangement of instances of a tile(s), in accordance with some embodiments of the present invention.

Reference is now made to FIG. 1A, which is a flowchart of a method for manufacturing a microstructure of a 3D object based on an arrangement of instances of a tile(s), in accordance with some embodiments of the present invention. FIG. 1B discussed below provides additional features to the method described with reference to FIG. 1A. Reference is also made to FIG. 2, which is a block diagram of a system 200 for manufacturing a microstructure of a 3D object based on an arrangement of instances of a tile(s), in accordance with some embodiments of the present invention. System 200 may generate code instructions according to the model, that when executed by a manufacturing device controller 202 cause a manufacturing device 202A to manufacture the microstructure of the 3D object. System 200 may execute the acts of the method described with reference to FIGS. 1A-1B, for example, by a hardware processor(s) 204 of a computing device 206 executing code 208A stored in a memory 208.

Manufacturing device 202A may be implemented as, for example, an additive manufacturing device for additive manufacturing of the microstructure, a 3D printer for 3D printing of the microstructure, a bioprinter for bioprinting of the microstructure, a fabrication machine for fabrication of the microstructure, a manufacturing device that manufactures parts for assembly by another device and/or parts that self assembly. The manufacturing device may implement different manufacturing methods, for example, based on a scallop, and/or template, and/or any combination of the aforementioned.

Manufacturing device controller 202 may be implemented as, for example, a hardware processor(s) integrated within manufacturing device 202A, and/or an external computing device in communication with manufacturing device 202A.

Computing device 206 may be implemented as, for example, a client terminal, a virtual machine, a server, a virtual server, a computing cloud, a mobile device, a desktop computer, a thin client, a kiosk, and a mobile device (e.g., a Smartphone, a Tablet computer, a laptop computer, a wearable computer, glasses computer, and a watch computer).

Multiple architectures of system 200 based on computing device 206 may be implemented. For example:

Computing unit 206 may be integrated with the manufacturing device (i.e., controlled by controller 202), for example, as a control console and/or control unit and/or instructions code stored within manufacturing device 202A for execution by a hardware processor(s) of the manufacturing device.

Computing device 206 may be implemented as a stand-alone device (e.g., kiosk, client terminal, smartphone) that include locally stored code instructions 208A that implement one or more of the acts described with reference to FIGS. 1A-1B. Computing device 206 is external to manufacturing device 202A, and communicates with manufacturing device 202A, for example, over a network, and/or by storing instructions on a data storage device that is then accessed by the controller. The locally stored instructions may be obtained from another server, for example, by downloading the code over the network, and/or loading the code from a portable storage device.

Computing device 206 executing stored code instructions 208A, may be implemented as one or more servers (e.g., network server, web server, a computing cloud, a virtual server) that provides services (e.g., one or more of the acts described with reference to FIGS. 1A-1B) to one or more client terminals 218 over a network 214. For example, providing software as a service (SaaS) to the client terminal(s) 218, providing software services accessible using a software interface (e.g., application programming interface (API), software development kit (SDK)), providing an application for local download to the client terminal(s) 218, providing an add-on to a web browser running on client terminal(s) 218, and/or providing functions using a remote access session to the client terminals 218, such as through a web browser executed by client terminal 218 accessing a web sited hosted by computing device 206.

Code 208A may be designed as an add-on to modeling, simulation, and/or analysis applications, for example, as a tool-bar, library, script, and/or additional menu features. For example, a commercial available simulation application may integrate code 208A to design the microstructure (as described herein), which then undergoes simulation by the commercially available simulation application. In another example, a commercially available analysis application may integrate code 208A to design the microstructure (as described herein), which then undergoes analysis and optionally manufacturing by the commercially available analysis application.

Hardware processor(s) 204 of computing device 206 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 204 may include a single processor, or multiple processors (homogenous or heterogeneous) arranged for parallel processing, as clusters and/or as one or more multi core processing devices.

Memory 208 stores code instructions executable by hardware processor(s) 204, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Memory 208 stores code 208A that implements one or more features and/or acts of the method described with reference to FIGS. 1A-1B when executed by hardware processor(s) 202.

Computing device 206 may include a data storage device 210 for storing data, for example, an application for use by a user to design the tile(s), the deformation map, and/or the geometric object, and/or a repository that stores the created models of the microstructure(s), and/or a repository that stores the generated instructions for execution by the manufacturing controller for manufacturing the microstructure. Data storage device 210 may be implemented as, for example, a memory, a local hard-drive, a removable storage unit, an optical disk, a storage device, and/or as a remote server and/or computing cloud (e.g., accessed using a network connection). It is noted that code instructions 208A may be stored in data repository 210, for example, with executing portions loaded into memory 208 for execution by processor(s) 204.

Computing unit 206 may include a data interface 212, optionally a network interface, for connecting to network 214, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing unit 206 may access one or more remote servers 216 and/or data storage device(s) 222 using network 214, for example, to obtain the definition of the tile, the deformation map, and/or the definition of the 3D object, and/or to provide the generated model of the microstructure of the 3D object and/or to provide the generate instructions for manufacturing of the microstructure.

Network 214 may be implemented as, for example, the internet, a local area network, a virtual network, a wireless network, a cellular network, a local bus, a point to point link (e.g., wired), and/or combinations of the aforementioned.

Computing device 206 may connect using network 214 (or another communication channel, such as through a direct link (e.g., cable, wireless) and/or indirect link (e.g., via an intermediary computing unit such as a server, and/or via a storage device) with one or more of:

Client terminal(s) 218, for example, when computing unit 206 acts as a server providing services to the client terminals.

An external manufacturing device controller 202 that controls manufacturing device 202A that manufactures the microstructure according to instructions based on the generated model of the microstructure.

A storage device 222 that stores the definition of the tile, and/or the deformation map (e.g., provided by client terminal 218, server 216, and/or used by computing device 206 for remote storage) and/or the generated model of the microstructure and/or the generate code instructions for manufacturing of the microstructure. Storage device 222 may include, for example, a storage server, a computing cloud storage server, or other implementations.

Server(s) 216 that may act as client terminals accessing computing device 206 for remote services, and/or data storage server(s) that store the definition of the tile, and/or the deformation map and/or the generated model of the microstructure and/or the generate code instructions for manufacturing of the microstructure.

Computing unit 206 includes or is in communication with a user interface 224 allowing a user to enter data and/or view presented data. Exemplary user interfaces 224 include, for example, one or more of, a touchscreen, a display, a keyboard, a mouse, and voice activated software using speakers and microphone.

Computing device 206 includes and/or is in communication with one or more physical user interfaces 224 that include a mechanism for a user to enter data (e.g., define the tile and/or the deformation map) and/or view the displayed results (e.g., the created model of the microstructure. Exemplary user interfaces 224 include, for example, one or more of, a touchscreen, a display, gesture activation devices, a keyboard, a mouse, and voice activated software using speakers and microphone. The user interface may present a graphical user interface (GUI) for entering the data and/or viewing the displayed results.

Referring now back to FIG. 1A, the method described with reference to FIG. 1A decouples the design of the macro- and the microstructures of a porous geometry of an object. The microstructure is modeled through a tile which is arranged within the domain of the deformation map. The macrostructure is modeled through trivariate deformation function which maps the arranged tiles from the parameter space to the object space. The method may create, for example, precise, water-tight geometries using functional composition.

Additional details of exemplary features may be found with reference to U.S. Utility application Ser. No. 15/919, 705 and/or Elber, G., 2016. *Precise construction of microstructures and porous geometry via functional composition. In: Proceedings of the 9th International Conference on Mathematical Methods for Curves and Surfaces.* pp. 108-125, by common inventors of the present application, incorporated herein by reference in their entirety.

At 110, a definition of a tile, optionally a 3D tile, is provided. The definition of the tile may be provided, for example, by a user manually creating the tile (e.g., using a GUI and/or tile design application), selected from predefined tiles stored in a dataset, randomly created by code executed by the processor(s) of the computing device, and/or automatically created according to bifurcated cells, as described herein in additional detail.

The tile may be defined, for example, as a univariate, a bivariate, a trivariate, and/or at higher dimensions, optionally trimmed.

The tile may be implicit and/or parametric.

The tile may include discontinuities.

The boundaries of the tile may be designed to comply with a defined $C^k$ connectivity requirement, to help ensure connectivity and/or smoothness of the tiles in the tile arrangement.

The tile may be freeform. The microstructure created by the instances of the tile (as described herein) is porous, including one or more apertures, lumens, and/or cavities.

A single tile may be defined, or multiple tiles. For example, each tile may be randomly generated (as described herein), which may result in each tile being unique. In another example, a set of tiles may be defined, for example, a set of 2, 4, 6, or other number of tiles. Tiles may be selected from the set, for example, bifurcated tiles with different degrees of bifurcation may be selected according to corresponding bifurcated cells, as described herein.

At 120, a deformation map, optionally a 3D and/or trivariate deformation map, that maps a parameter space to a Euclidean space of an object, optionally a 3D object, is defined.

The definition of the deformation map may be provided, for example, by a user manually creating the deformation map (e.g., using a GUI and/or deformation map design application), selected from predefined deformation maps stored in a dataset, and/or created according to a definition of the 3D object.

The tile(s) and/or deformation map may be defined, for example, as a Bézier, and/or a B-spline/NURBs freefrom.

At 130, the instances of the trivariate tile are arranged within at least a portion of a domain of the trivariate deformation map to create a tile arrangement.

The process of arranging the tiles is sometimes referred to as paving.

The instances may be of the same tile, and/or may each be of a different tile, for example, when each tile is randomly created, and/or may be selected from a set of defined tiles, for example, when the deformation map is subdivided to include bifurcation cells and the defined tiles include bifurcation tiles.

Optionally, one or more freeforms (i.e., surfaces or faces) of each of the instances of the tile coincide and are connected with one or more other freeforms of another of the instances of the tile, creating continuity and/or smoothness between the instances of the 3D tile.

Optionally, the instances of the tile(s) are arranged within the entire domain of the trivariate deformation map. The instances of the tile(s) are contained within the domain of the trivariate deformation map.

Optionally, the tile(s) are placed in respective cells of a grid, optionally a 3D grid, of the domain of the trivariate deformation map. Cells may be cubes, rectangles, or other shapes. The cells may be arranged regularly, where each interior cell is in contact with neighboring cells, for example, interior cube cells are in contact with 6 neighboring cubes. The tile located within each respective cell is mapped according to the trivariate deformation map corresponding to the respective cell.

At 140, a representation of the object having a microstructures is created by composing the tile arrangement into the trivariate deformation map, optionally by a functional composition process.

Optionally, the representation of the microstructures is smooth, even when random tiles are utilized, as described herein. The smooth representation of the microstructure, when manufactured, produces a smooth physical microstructures.

The representation of the object having the microstructure is computed by a functional composition of a tile function(s) representing the respective tile and the portion of the trivariate deformation map corresponding to the respective tile. Alternatively or additionally, the functional composition is of function(s) representing the arrangements of the multiple tiles and the trivariate deformation map (e.g., the entire map). Additional details of functional decomposition are discussed, for example, with reference to DeRose, T. D., Goldman, R. N., Hagen, H., Mann, S., April 1993. *Functional composition algorithms via blossoming. ACM Trans. Graph.* 12 (2), 113-135 and Elber, G., 1992. *Free Form Surface Analysis Using A Hybrid of Symbolic and Numerical Computation.* PhD Thesis, University of Utah.

In terms of mathematical representation, given (i) a deformation map $\mathcal{D}: \mathbb{R}^3 \to \mathbb{R}^3$ and (ii) a tile, $T \in \mathbb{R}^3$, a functional composition operation algebraically computes the image of T through $\mathcal{D}$, i.e., $\mathcal{D}(T)$. It is noted that the Bézier and/or B-spline representation for T and/or $\mathcal{D}$ is exemplary, and not necessarily limiting. The composition of a trivariate tile, given in Bézier and/or B-spline form, into a trivariate deformation map, given in Bézier is now described in mathematical terms. The trivariate deformation map is mathematically represented as:

$$\mathcal{D}(x, y, z) = \sum_{i_1=0}^{n_1} \sum_{i_2=0}^{n_2} \sum_{i_3=0}^{n_3} P_{i_1, i_2, i_3} B_{i_1}^{n_1}(x) B_{i_2}^{n_2}(y) B_{i_3}^{n_3}(z)$$

Where:

$P_{i_1 i_2 i_3}$ denote the control points of $\mathcal{D}$ $B_{i_1}^{n_1}(x)$, $B_{i_2}^{n_2}(y)$, $B_{i_3}^{n_3}(z)$ denote the Bézier basis functions.

The trivariate tile is mathematically represented as:

$$T(u, v, w) = \sum_{j_1=0}^{m_1} \sum_{j_2=0}^{m_2} \sum_{j_3=0}^{m_3} Q_{j_1, j_2, j_3} B_{j_1}^{m_1}(u) B_{j_2}^{m_2}(v) B_{j_3}^{m_3}(w)$$

Where $Q_{j_1 j_2 j_3}$ denote the control points of T.

The functional composition of the tile and the deformation map is mathematically represented as:

$$\bar{T} = \mathcal{D}(T) = \mathcal{D}(t^x(u, v, w), t^y(u, v, w), t^z(u, v, w)) =$$

$$\sum_{i_1=0}^{n_1} \sum_{i_2=0}^{n_2} \sum_{i_3=0}^{n_3} P_{i_1, i_2, i_3} B_{i_1}^{n_1}(t^x(u, v, w)) B_{i_2}^{n_2}(t^y(u, v, w)) B_{i_3}^{n_3}(t^z(u, v, w)),$$

where $(t^x, t^y, t^z)$ denote the control coefficients of T.

When the coefficients of control point $Q_{i_1 i_2 i_3}$ are denoted by $(q_{j_1 j_2 j_3}^x, q_{j_1 j_2 j_3}^y, q_{j_1 j_2 j_3}^z)$, then the composition $B_{i_1}^{n_i}(t^x(u,v,w))$ may be computed according to the following mathematical relationships:

$$B_{i_1}^{n_1}(t^x(u, v, w)) = \binom{n_1}{i_1} t^x(u, v, w)^{i_1} (1 - t^x(u, v, w))^{n_1 - i_1} =$$

$$\binom{n_1}{i_1} \left( \sum_{j_1=0}^{m_1} \sum_{j_2=0}^{m_2} \sum_{j_3=0}^{m_3} q_{j_1, j_2, j_3}^x B_J^M(u, v, w) \right)^{i_1}$$

$$\left( 1 - \sum_{j_1=0}^{m_1} \sum_{j_2=0}^{m_2} \sum_{j_3=0}^{m_3} q_{j_1, j_2, j_3}^x B_J^M(u, v, w) \right)^{n_1 - i_1}$$

Where $B_J^M(u, v, w) = B_{j_1}^{m_1}(u) B_{j_2}^{m_2}(v) B_{j_3}^{m_3}(w)$.

The functional compositions for $B_{i_2}^{n_2}(t^y)$ and $B_{i_3}^{n_3}(t^z)$ may be performed similarly. The product of Béziers or B-spline basis function in the above mentioned equation may be performed precisely, for example, as described with reference to Elber, G., 1992. *Free form surface analysis using a hybrid of symbolic and numerical computation.* PhD Thesis, University of Utah, Farin, G., 1993. *Curves and Surfaces for Computer Aided Geometric Design. Academic Press Professional,* Boston, and Farouki, R. T., Rajan, V. T., June 1988. *Algorithms for polynomials in Bernstein form. Comput. Aided Geom. Des.* 5 (1), 1-26. The functional composition of univariate and/or bivariate geometries into trivariate tiles may be performed in a similar way.

At 150, the created representation of the object having the microstructure is stored in a format designed for generating code instructions for execution by a manufacturing device controller for manufacturing the representation of the object having the microstructure and/or stored in a format for analysis and/or simulation thereof.

For example, the created representation may be stored as a file readable by a compiler that translates the file into code instructions for execution by the manufacturing device. The created representation may be, for example, locally stored on the computing device, transmitted to a remote storage server and/or remote storage device, and/or stored by the client terminal accessing the computing device.

The representation of the microstructure may be further processed, without necessarily being manufactured. For example, the microstructure may be generated to model structures, for example, bones. Modeling may be performed to simulate and/or analyze (e.g., compute rigidity and/or stability of) the microstructures, optionally in response to external forces (e.g., effect of body mass on bone stability). The microstructure may be adjusted according to the simulation and/or analysis, for example, to increase rigidity and/or stability. The modeled and/or simulated and/or analyzed microstructure may or may not be manufactured.

At 160, code instructions for execution by the manufacturing device controller for manufacturing the representation of the object having the microstructure are generated. The code instructions may be generated, for example, by a compiler, by the manufacturing device controller, by the client terminal, by the computing device, and/or by a remote server.

At 170, a physical object having the microstructure is manufacturing according to the manufacturing device controller executing the code instructions.

A tangible microstructure may be manufactured based on the computed representation. The microstructure may be manufactured, for example, in 2D (e.g., as a 2D-manifold, and/or a 2D structure on a surface), in 3D, and/or in 4D. Examples of manufacturing devices include: an additive manufacturing device for additive manufacturing of the microstructure, a 3D printer for 3D printing of the microstructure, a bioprinter for bioprinting of the microstructure, a fabrication machine for fabrication of the microstructure, a manufacturing device that manufactures parts for assembly by another device and/or parts that self assembly. The manufacturing device may implement different manufacturing methods, for example, based on a scallop, and/or template, and/or any combination of the aforementioned.

Figure 21:
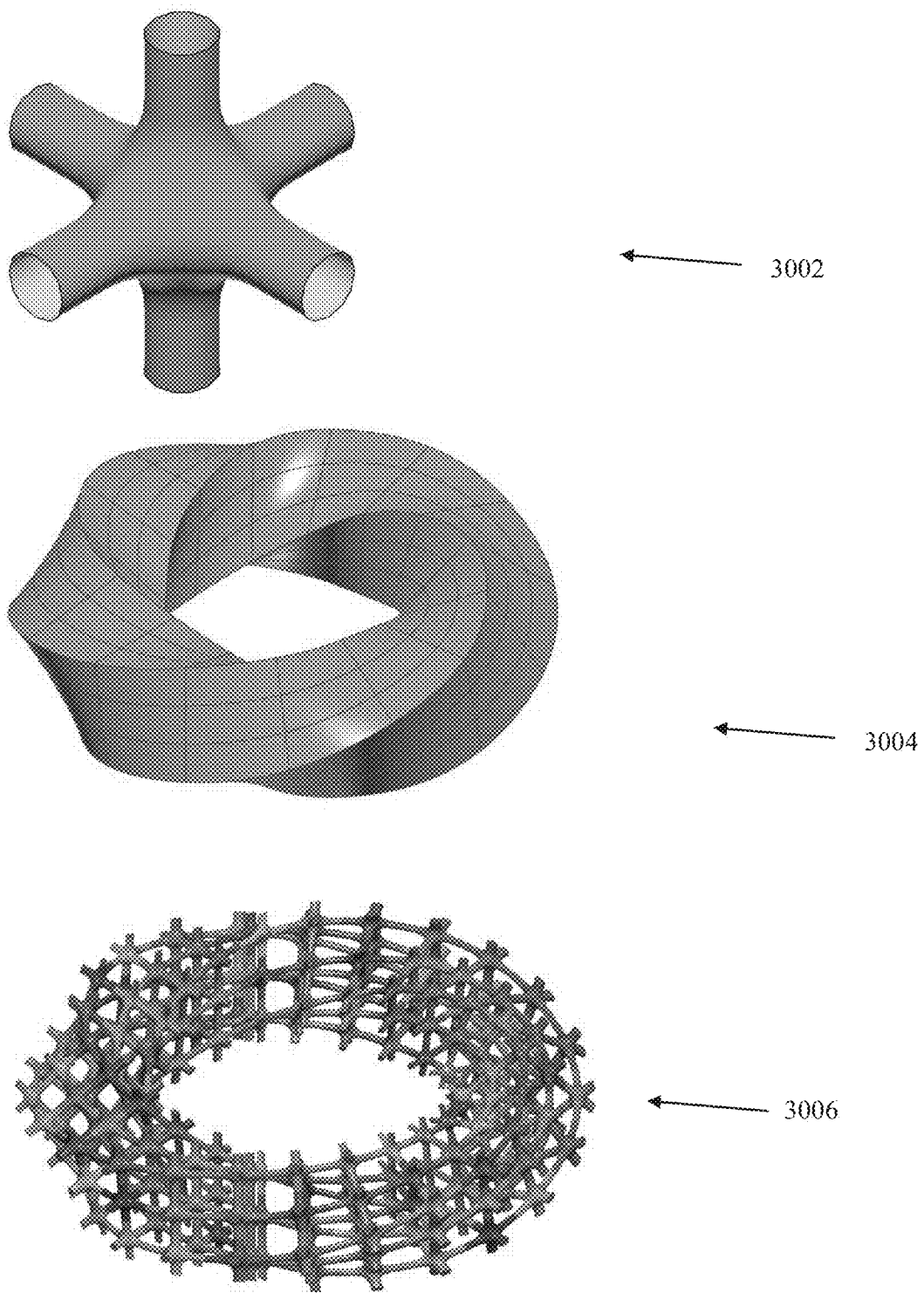
FIG. 21 is a schematic depicting the process of creating the representation of the microstructure, in accordance with some embodiments of the present invention.

Reference is now made to FIG. 21, which is a schematic depicting the process of creating the representation of the microstructure, in accordance with some embodiments of the present invention. A definition of a tile 3002, and a deformation map 3004 are provided. A microstructure 3006 is created by arranging multiple instances of tile 3002 within the domain of deformation map 3004 to create a tile arrangement, and composing the tile arrangement with deformation map 3004, as described herein.

Reference is now made to FIG. 1B, which is a flowchart of one or more additional features for computing a model of a microstructure of a 3D object based on at least one definition of a tile and a deformation map, in accordance with some embodiments of the present invention. The additional features are described with reference to the method described with reference to FIG. 1A.

At 110, the tile is provided, as described with reference to FIG. 1A.

Optionally, random tiles are created. The random tiles may be computed as part of a process of designing irregular randomized microstructures that are $C^1$ continuous. An analysis to ensure connectivity of the random tiles is discussed below.

At 112, one branch-in surfaces and/or one or more branch-out surfaces are defined for the tile. Each tile may include multiple boundary surfaces (also referred to herein as faces). The branch-in surface and branch-out surfaces define a hierarchical tile structure for creation of a hierarchical microstructure.

Optionally a single branch-in surface is defined, and/or two or more branch-out surfaces are defined. The surfaces may be defined for the reference tile when the same tile is copied into multiple instances. Tiles with two or more branch-out faces are said to have a bifurcation, for example, as described with reference to Rozenberg, G., Salomaa, A., 1992. *Lindenmayer Systems: Impacts on Theoretical Computer Science, Computer Graphics, and Developmental Biology*. Springer.

Optionally, the two or more branch-out surfaces are based on a geometric bifurcation of the tile created by a partial Euclidean discontinuity of the tile. The partial Euclidean discontinuity leads to a geometric split within the tile, which results in the bifurcation of the tile. A tile with n discontinuities along any direction has n+1 branches along that direction. For simplicity and clarity of explanation without necessarily limiting, it may be assumed that the discontinuities in the trivariate tiles are along the u and/or v directions. Hence, a tile with n and m discontinuities along the u and v directions, respectively, will have, in all, (n+1)(m+1) branches. The instructions for arranging the tiles into the hierarchical tile arrangement may be implicitly encoded within the discontinuities of the tile.

Alternatively or additionally, the single branch-in surface and each of the at least two branch-out surfaces are designated according to boundary surfaces of the 3D tile. The created hierarchical tile arrangement and/or hierarchical microstructure may represent a fractal-like structure. The instructions for creating the hierarchical arrangement may be explicitly encoded within the tile.

The branch-in and branch-out surfaces are mappable, and/or related to one another by a map. The branch-out surface(s) may be the same as the branch-in surface(s), up to some (optionally simple) mapping. Optionally, an affine transform maps the branch-in face to each of the branch-out faces. A tile with n branch-out faces may have n such affine transforms.

The surfaces may be defined for example, by manual user selection (e.g., via a GUI), based on predefined surface definitions (e.g., when the tile is selected from a set of predefined tiles), and/or automatically selected by code.

The instances of the tile with the defined surfaces may be are arranged within the domain of the deformation map to create the tile arrangement (e.g., as described with reference to act 130) by iteratively mapping the respective single branch-in surface of each of respective tile at a next level to a respective branch-out surface of each respective tile at a current level. The iterative arrangement of the tiles creates a hierarchical tile microstructure. It is noted that when the tiles are iteratively arranged according to the branch-in and branch-out surface, the tiles are not necessarily placed in a 3D regular grid, but may be placed in a hierarchical grid.

Optionally, for the same tile, the surface area of the single branch-in surface is larger than the surface area of each of the branch-out surfaces. In order to provide a smooth continuity between tiles of the current level and tiles of the next level, the size of the tile of the next level is adjusted (e.g., reduced) such that the surface area of the single branch-in surface matches (i.e., coincides with) the area of one of the branch-out surfaces to create continuity between the tile of the current level and the tile of the next level.

The iterations for arranging the 3D tiles may be performed for a predefined number of tile levels. The number of levels may be selected for filling the domain of the deformation map. Alternatively or additionally, the number of levels may be selected with other considerations, for example, to reach a certain surface area to volume ratio, for example, when designing a heat sink. The number of levels may be selected, for example, manually entered by a user (e.g., via the GUI), obtained from a predefined system parameter, and/or automatically computed by code (e.g., selected to fill the domain of the deformation map).

Optionally, the next layer of 3D tiles is approximated by reducing degrees of polynomial functions representing the next layer of 3D tiles.

Figure 3:
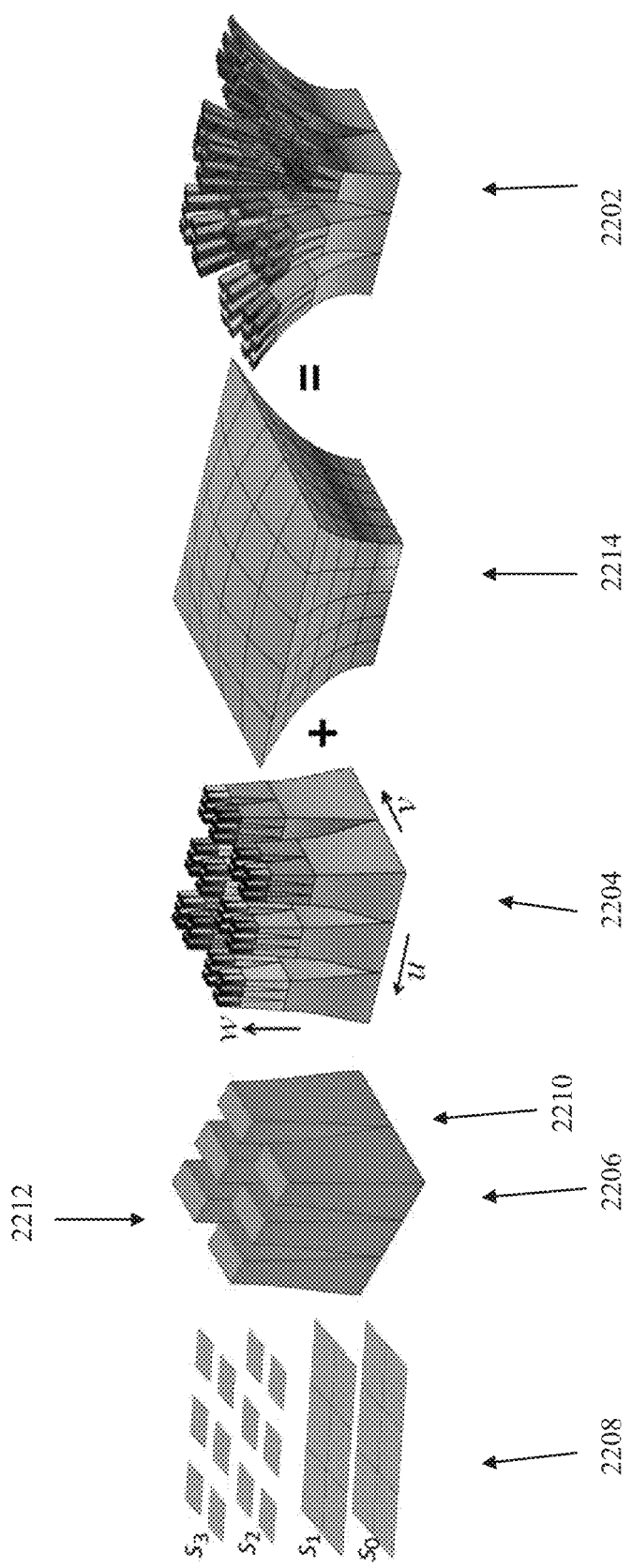
FIG. 3 is a schematic depicting creation of a hierarchical microstructure according to an iterative tile arrangement of a tile with discontinuities, in accordance with some embodiments of the present invention.

Reference is now made to FIG. 3, which is a schematic depicting creation of a hierarchical microstructure 2202 according to an iterative tile arrangement 2204 of a tile with discontinuities 2206, in accordance with some embodiments of the present invention. Tile 2206 is represented as a trivariate having two discontinuities along u and one discontinuity along v. Tile 2206 is created by skinning through surfaces $S_0$, $S_1$, $S_2$, and $S_3$ (denoted by arrow 2208). $S_2$ and $S_3$ include discontinuities. Tile 2206 includes a single branch-in surface 2210 (i.e., the bottom surface) and 6 branch-out surfaces 2212 (i.e., the top surfaces). Tile arrangement 2204 is created by iteratively mapping the bottom branch-in surface of each tile at a higher level to each of the branch-out surfaces of each tile at the bottom layer. Three levels are shown. Tile arrangement 2204 is composed into a deformation map 2214 to create hierarchical microstructure 2202. The degrees of tile 2210, deformation map 2214 and hierarchical microstructure 2202 in (u, v, w) are (2, 2, 3), (2, 2, 2) and (12, 12, 18) respectively.

Figure 4:
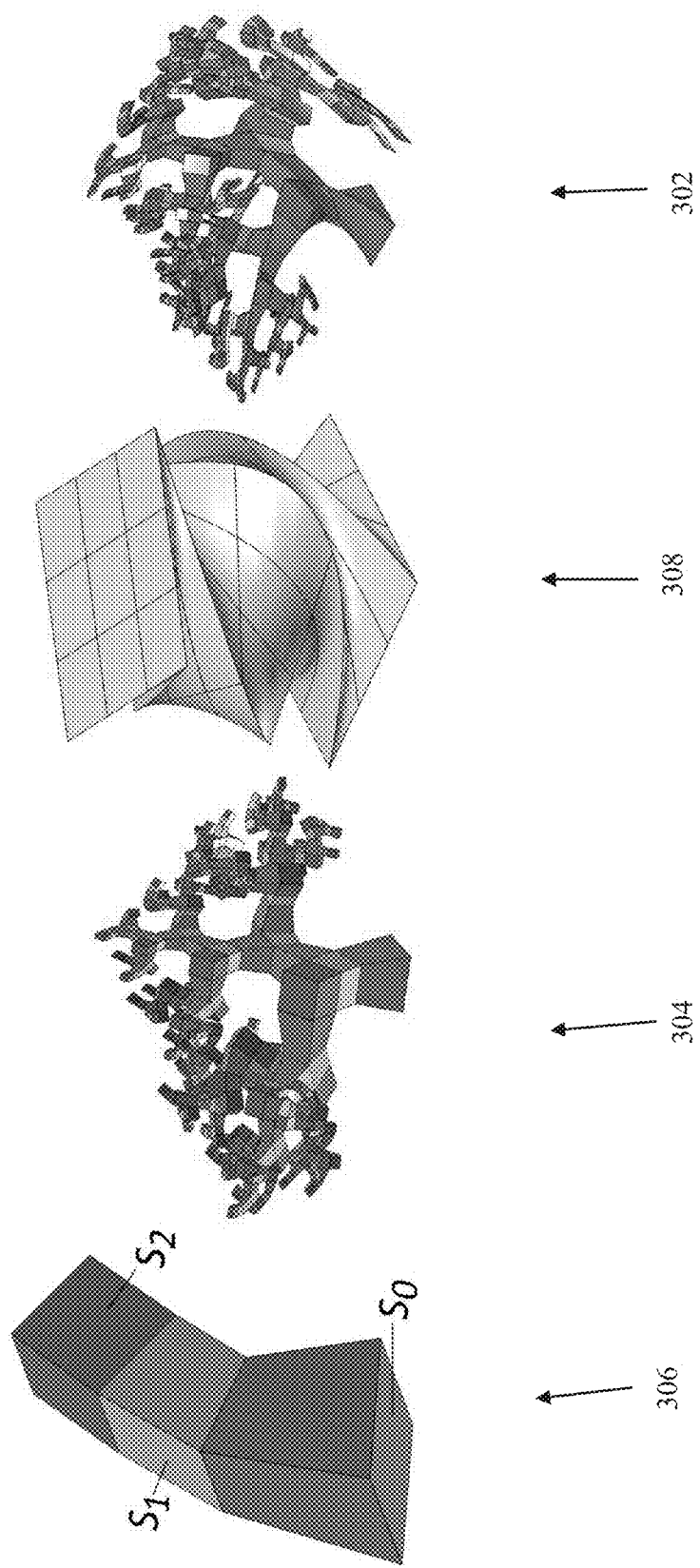
FIG. 4 is a schematic depicting creation of a hierarchical microstructure according to an iterative tile arrangement of a tile (i.e., without discontinuities) with designated surfaces, in accordance with some embodiments of the present invention.

Reference is now FIG. 4, which is a schematic depicting creation of a hierarchical microstructure 302 according to an iterative tile arrangement 304 of a tile 306 (i.e., without discontinuities) with designated surfaces, in accordance with some embodiments of the present invention. Tile 306 is represented according to three trivariate element. The boundary surface $S_0$ is designated as a branch-in surface, Boundary surfaces $S_1$ and $S_2$ are designated as branch-out surfaces. Tile arrangement 304 is created by iteratively (i.e., recursively) mapping the branch-in surface of each tile at a higher level to each of the branch-out surfaces of each tile at the bottom layer. Seven levels are shown. Tile arrangement 304 is composed into a deformation map 308 to create hierarchical microstructure 302. The degrees of tile 306, deformation map 308 and hierarchical microstructure 302 in (u, v, w) are (1, 1, 1), (3, 3, 2) and (8, 8, 8) respectively.

Referring now back to FIG. 1B, At 120, the deformation map is provided, as described with reference to FIG. 1A.

At 122 of FIG. 1B, optionally the 3D tile is further associated with one or more material parameters. For example, by an additional set of coordinates of the tile. For example, the trivariate tile may be represented as a vector function $(x, y, z, c_1, \ldots, c_n)$, where $x, y, z, c_1, \ldots, c_n$, are the coefficients of the trivariate. The parameters $x, y, z$ denote coordinates representing the geometry of the tile. The parameters $c_1, \ldots, c_n$ represent material properties.

The material parameters may be defined before and/or after the tile is arranged within the deformation map, and/or after the tile is composed into the deformation map to create the microstructure.

The deformation map may include instructions for adjustment of material parameters. When the deformation map is applied to the arranged instances of the tile (e.g., by functional composition, as described herein), the material parameters associated with each tile is adjusted (e.g., mapped) according to the portion of the deformation map corresponding to the respective instance of the tile, for example, the cell of the deformation map within which the tile is located. Tiles defined with the same parameters may map to different resulting material properties of the representation of the microstructure.

For example, the deformation map may include instructions to increase the strength of the material at weak and/or critical locations, for example, by increasing the density and/or thickness of the material. The same tile with the same defined material parameters may be used to construct a microstructure with heterogeneous material properties. Alternatively, the deformation map does not include instructions for adjustment of the material properties of the tile. In such a case, the material properties of the tile are unaffected by composition with the deformation map.

Optionally, the material properties and/or instructions for adjustment of the material properties are stored in the parameter space of the deformation map.

The material parameters of the tile and/or the deformation map may be set, for example, manually by the user (e.g., selected via the GUI), selected from a set of available parameters, and/or automatically computed by (analysis) code.

At 124 of FIG. 1B, a non-grid topology may be created by subdividing the domain of the trivariate deformation map into multiple cells, optionally based on a process of non-regular adaptive subdivision. Each tile located in each respective cell is composed by the respective corresponding subdivision of the domain of to approximately the same size in object (e.g., Euclidean) space. The phrase approximately the same size in object (e.g., Euclidean) space may be according to a tolerance requirement, where tiles of cells that are mapped to a defined tolerance range of sizes are considered as being mapped to approximately the same size in object (e.g., Euclidean) space. The tolerance may be set, for example, as less than about 110%, or 120%, or 150% of a reference size of a tile mapped to the object space.

The division of the domain of the deformation map to include bifurcation cells may be performed when a regular grid creates vast differences in tile sizes. A regular grid, which may include the same number of cells in each layer and/or where each tile has at most one neighboring tile in each direction, may define a uniform size for each cell in the domain of the deformation map. However, after the uniform sized tiles in the uniformed sized cells are mapped by (i.e., composed into) the deformation map to create the representation of the microstructure, the sizes of the tiles of the microstructure may vary significantly due to non-isometric behavior of the deformation map. The division of the domain of the deformation map may form tiles that preserve uniform size when mapped by (i.e., composed into) the divided deformation map to create the representation of the microstructure.

Optionally, the domain of the deformation map, for example the trivariate deformation map, is divided to include bifurcation cells. The division into the bifurcation cells may be according to provided bifurcation tiles.

An exemplary method of dividing the domain of the deformation map into bifurcation cells is now described. Given a deformation map D, the topology of the tiling may be adaptively built by subdividing the parametric space of D until each cell satisfies a certain condition on D. The determinant of the Jacobian of D mathematically denoted $|J|=$ $$|J| = \left(\frac{\partial \mathcal{D}}{\partial u} \times \frac{\partial \mathcal{D}}{\partial v} + \frac{\partial \mathcal{D}}{\partial w}\right)$$

is an exemplary and not necessarily limiting classification condition. However, $|J|$ does not hint on the preferred direction to subdivide.

Another exemplary process is now described for dividing the domain of the deformation map into bifurcation cells: Given a sub-domain d, of D, and an object (e.g., Euclidean) space subdivision threshold $\varepsilon$, the image of d's eight corner points under D. Let e be the edge of d with the maximal length under D's image. When $|e|>\varepsilon$, d is subdivided at the middle of its parametric domain, in the direction of e. Otherwise, the subdivision process terminates. The adaptive topological bifurcation process is initialized with the call TopoSubdiv(D, d, $\varepsilon$), i.e. FIG. 5.

Reference is now made to FIG. 5, which includes pseudo code of a process of performing topological subdivision of a domain of a deformation map, in accordance with some embodiments of the present invention.

Figure 6:
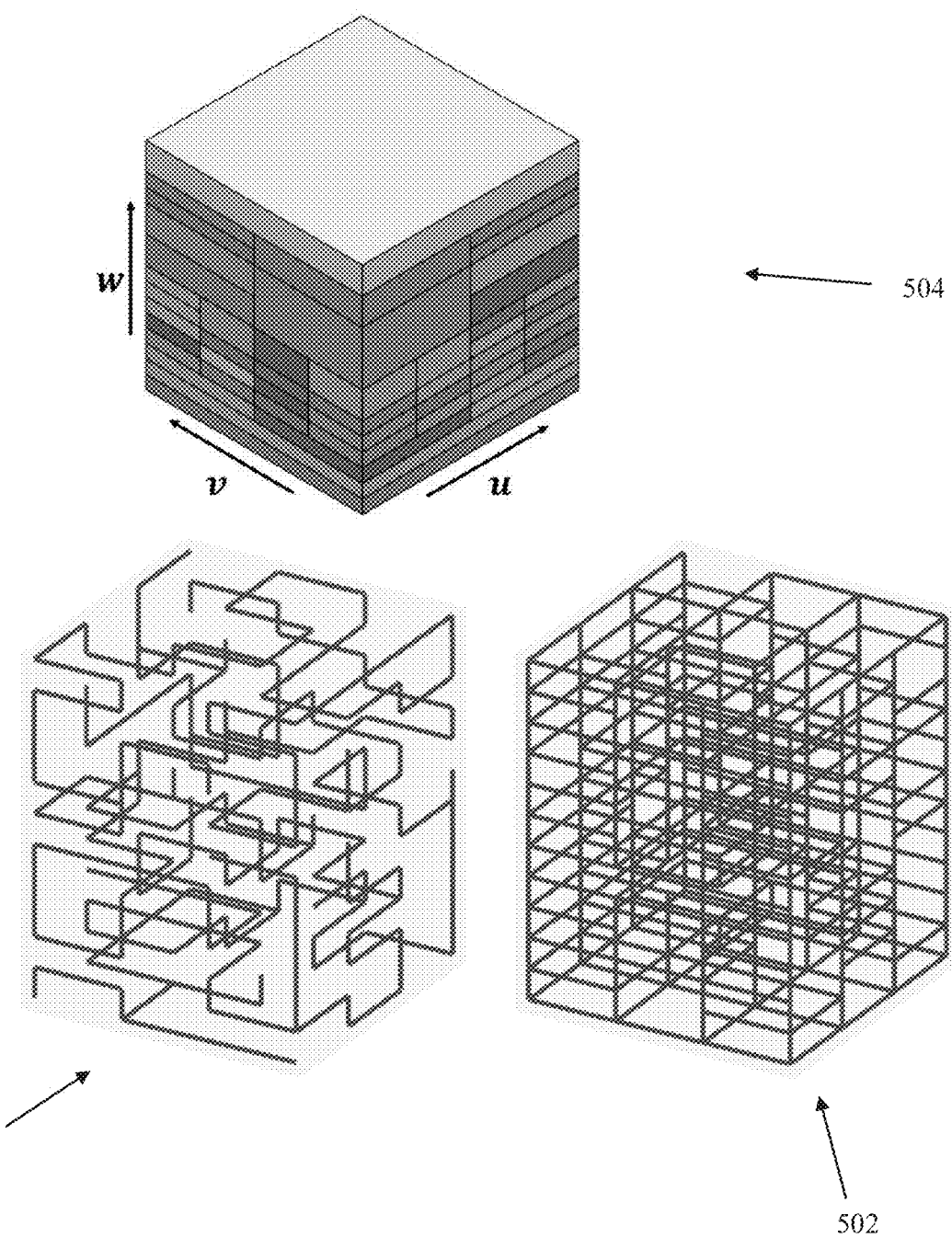
FIG. 6 is a schematic of an example of a domain of a deformation map including adaptive topological bifurcations created as described herein, in accordance with some embodiments of the present invention.

Reference is now made to FIG. 6, which is a schematic of an example of a domain of a deformation map 504 including adaptive topological bifurcations created as described herein, in accordance with some embodiments of the present invention. Deformation map 504 with bifurcated cells is used to create duck microstructure 1502 depicted in FIG. 18, and duck microstructures 1602B-C depicted in FIG. 19. The deformation map 504 is subdivided according to the process described with reference to FIG. 5. Where $\varepsilon=0.35$, and the length of the duck is a little over 2. The w direction starts from the tail of the ducks and ends at the head of the ducks. A connectivity graph 506 is computed according to the tiles arranged according to divided deformation map 504. Connectivity graph 506 includes the first spanning tree. Connectivity graph 502 includes the first and second spanning trees.

Referring now back to FIG. 1B, at 126, alternatively and/or additionally to the process of dividing the domain of the deformation map into bifurcation cells according to provided bifurcation tiles, bifurcated tiles may be automatically computed according to bifurcation cells created by the subdivision of the domain of the trivariate deformation map. Bifurcation tiles may be generated for implicit microstructures and/or for parametric microstructures.

An exemplary method for generating bifurcation tiles for implicit microstructures is now described. For a cell denoted C, located within a topological subdivision denoted G (e.g., computed based on the process described with reference to FIG. 5), each surface of C may be topologically classified as one of the following exemplary classifications:

1. A boundary face of G.
2. Identical to a neighbor cell face. Such is the case where at the certain face there is only one neighboring tile.
3. A complex of multiple faces. Such is the case where bifurcation is performed along the direction of the certain face.

When all the faces of C are of the first or second type, then C is considered a simple cell and the trivariate defining its tile may be randomly constructed, for example, as described herein with reference to act 110. When C has at least one complex face of the third type, then the cell is considered as a bifurcation cell. The implicit trivariate for the bifurcation cell may be created according to the following exemplary process:

1. Build 6 boundary B-spline surfaces, one surface for each face. For a simple face (classification type 1 or 2) the coefficients of the trivariate on the respective face are assigned random values, for example, according to the mathematical relationship $p_{i,j,k}=(1-\alpha)p_{i,j,k}^0+\alpha$Random$(-1,1)$, as described herein. When the face is complex (i.e., classification type 3), all the neighboring surfaces (i.e., that are already constructed) are merged into a single B-spline surface.

Figure 7:
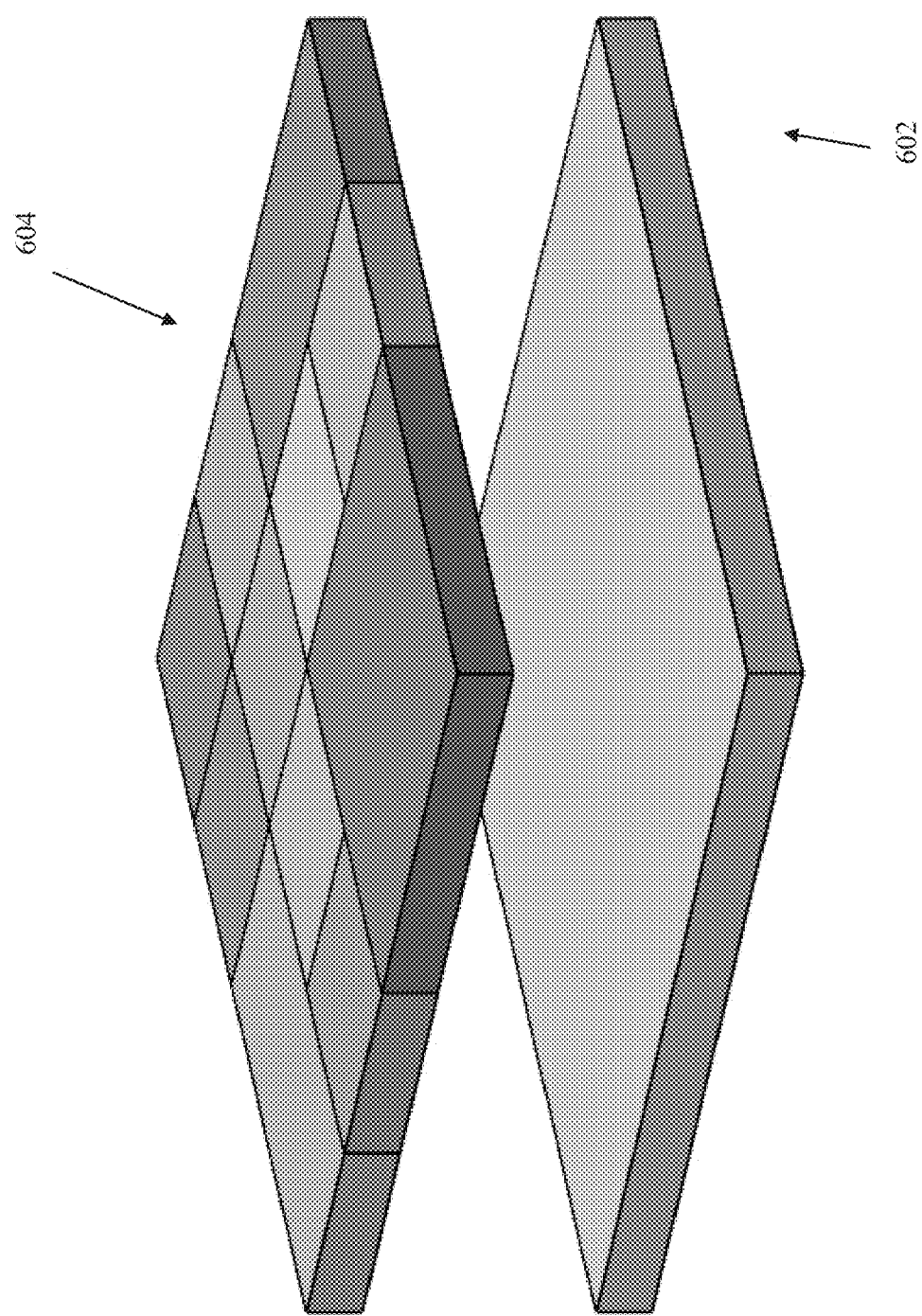
FIG. 7 is a schematic depicting an example of a highly complex face, and neighboring faces, in accordance with some embodiments of the present invention.

Reference is now made to FIG. 7 which is a schematic depicting an example of a highly complex face 602, and neighboring faces 604, in accordance with some embodiments of the present invention. The neighboring faces 604 are stitched recursively along their shared edges to construct a single B-spline surface corresponding to (i.e., the same as) complex face 602.

2. Construct a trivariate, using volumetric Boolean sum (e.g., as described with reference to Elber, G., Kim, Y-J., Kim, M.-S., 2012. *Volumetric boolean sum. Computer Aided Geometric Design* 29 (7), 532-540, *geometric Modeling and Processing* 2012), over the 6 faces of Step 1.

Figure 8:
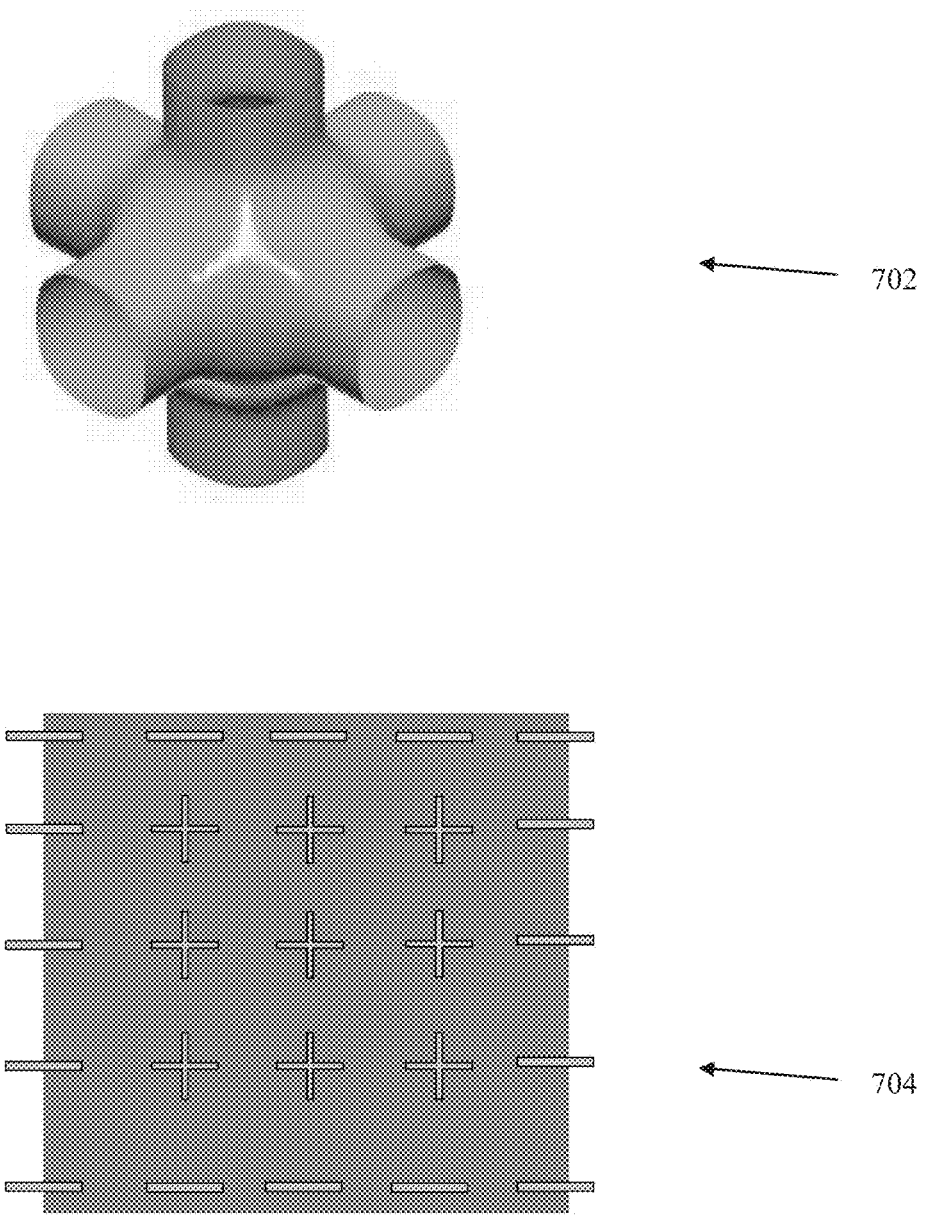
FIG. 8 is a schematic of a tile constructed as the zero set of the volumetric Boolean sum trivariate of six B-spline surfaces having a coefficient pattern having negative values on the boundaries and positive values in the interior, in accordance with some embodiments of the present invention.

Reference is now made to FIG. 8, which is a schematic of a tile 702 constructed as the zero set of the volumetric Boolean sum trivariate of six B-spline surfaces having a coefficient pattern 704, having negative values on the boundaries and positive values in the interior, in accordance with some embodiments of the present invention. It is noted that the construction method used to construct tile 702 is also used to construct the tiles of duck 1602B depicted in FIG. 19.

3. Randomize the internal coefficients of the trivariate from Step 2 according to randomization the randomization factor $\alpha$ of the mathematical relationship $p_{i,j,k}=(1-\alpha)p_{i,j,k}^0+\alpha$Random$(-1, 1)$. $C^1$ connectivity between the tiles may be ensured, for example, as described with reference to act 132.

An exemplary method for generating bifurcation tiles for parameteric microstructures is now described. It is noted that for parametric tiles, automatically creating the bifurcation tiles for arbitrary general topology may be complex. Hence, tiles with proper connectivity and/or continuity conditions may be a-priori defined. A set of bifurcation tiles may be provided, for example, manually created by the user (e.g., via the GUI), automatically created by code, and/or obtained from a predefined set such as available default. Each bifurcation tiles is classified according to its respective bifurcation topology. For instance, 1 to 2 connection, and 1 to 4 connections. Based on the topology of the bifurcation tiles provided, the divided structure (e.g., described with reference to FIG. 5) is restricted to subdivisions that respectively conform to each of the bifurcation tiles. Based on the example tile set, the bifurcation is restricted to be along layers in one direction, and allow only three types of bifurcations: 1 to 2 and two types of 1 to 4.

Figure 9:
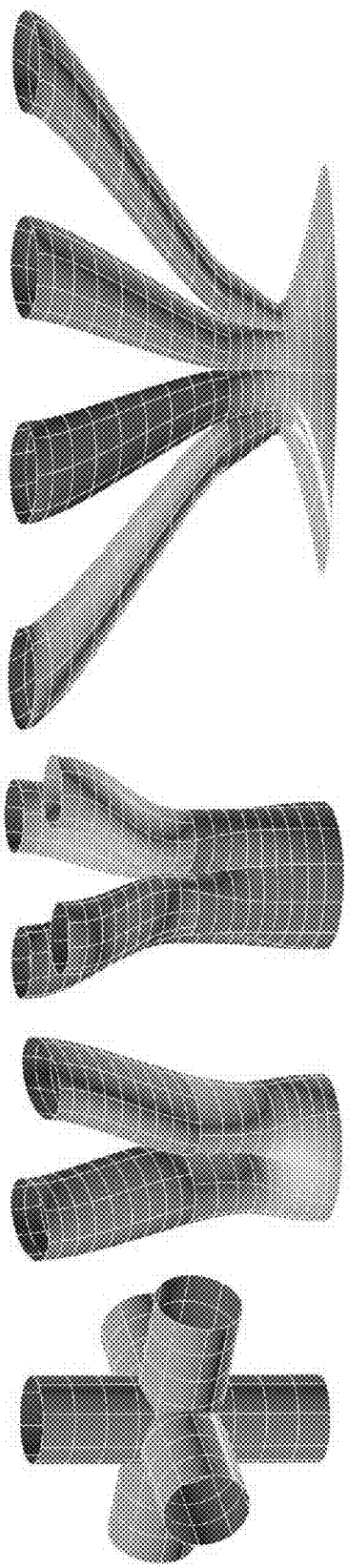
FIG. 9 is an example of bifurcation tiles, formed out of tensor product B-spline surfaces, in accordance with some embodiments of the present invention.

Reference is now made to FIG. 9, which is an example of parameteric bifurcation tiles, formed out of tensor product B-spline surfaces, in accordance with some embodiments of the present invention.

Referring now back to FIG. 1B, at 130, the tiles are arranged within the domain of the deformation map to create the tile arrangement, as described with reference to act 130 of FIG. 1A.

An exemplary method of arranging random tiles to create a continuous and/or smooth tile arrangement is now described.

For a 3D grid of the deformation map, where the grid includes $m_x$, $m_y$, $m_z$ cells in the x, y, z direction respectively, a random tile is created in each cell. For each cell $C_{qrs}$, $0 \le q < m_x$, $0 \le r < m_y$, $0 \le s < m_z$, a scalar tensor product trivariate B-split function $f^{qrs}(x, y, z)$ is denoted:

$$f^{qrs}(x, y, z) = \sum_{i=0}^{n_x} \sum_{j=0}^{n_y} \sum_{k=0}^{n_z} p_{i,j,k} B_{i,d_x}(x) B_{j,d_y}(y) B_{k,d_z}(z)$$

Where:
$f^{qrs}$ defined over the box domain of $C_{qrs}$: $[X_{min}, X_{max}) \times [Y_{min}, Y_{max}) \times [Z_{min}, Z_{max})$,
$p_{i,j,k} \in [-1, 1]$, $0 \le i \le n_x$, $0 \le j \le n_y$, $0 \le k \le n_z$, are the control coefficients of $f^{qrs}$,
$B_{i,d}$ denotes the i'th univariate B-spline basis functions of degree d, with an open end knot sequence.

The tile in cell $C_{qrs}$ denotes the implicit function $f^{qrs}(x, y, z)=0$. $f^{qrs}$ is positive inside the tile and negative outside the tile.

The following design parameter may be set, for example, manually by a user (e.g., via the GUI), according to predefined configuration settings, and/or automatically by code:

The degrees $d_x$, $d_y$, $d_z$, and number of control coefficients, $n_x$, $n_y$, $n_z$ for $f^{qrs}$ in each direction for every cell.

A canonical trivariate $f_0^{qrs}$, that is in the same function space as $f^{qrs}$.

A randomization factor, $\alpha \in [0,1]$, that controls the randomness of $f^{qrs}$ relative to $f_0^{qrs}$. For $\alpha=0$, $f^{qrs}=f_0^{qrs}$, and for $\alpha=1$, the coefficients $p_{i,j,k}$ of $f^{qrs}$ are completely random.

The coefficients $p_{i,j,k}$ of $f^{qrs}$ are denoted as:

$p_{i,j,k}(1-\alpha)p_{i,j,k}^0+\alpha$Random$(-1,1)$ where:
$p^0_{i,j,k}$ denote the coefficients of $f_0^{qrs}$
Random$(-1,1)$ denotes a random number in the domain $[-1,1]$.

A zero set approximation of the geometry of the implicit function $f^{qrs}(x, y, z)=0$ may be extracted, for example, according to the marching cubes process, for example as described with reference to Lorensen, W. E., Cline, H. E., August 1987. *Marching cubes: A high resolution 3d surface construction algorithm. SIGGRAPH Comput. Graph.* 21 (4).

Defining a $C^1$ smooth trivariate $f^{qrs}$ creates a $C^1$ smooth tile, in general, however, smoothness between tiles is not necessarily guaranteed.

Optionally, when each tile is randomly generated and placed within a respective cell of a 3D grid of the domain of the deformation map, the tiles may be randomly generated according to similar control coefficients along common boundaries of respective cells of the grid to create continuity and/or smoothness between adjacent randomly generated tiles. For example, at each boundary of the cell, $C^0$ continuity may be obtained by verifying that the trivariates in neighboring cells share similar control coefficients along their common boundary. $C^1$ continuity may be obtained by placing the first inner layer of control coefficients from both sides of the common boundary at same distance from the shared control coefficients on the boundary between the cells. For example, for two cells denoted $C_{q,r,s}$ and $C_{q+1,r,s}$ having control coefficients $p_{ijk}$ and $q_{ijk}$, respectively. $C^0$ continuity implies (for the yz boundary face):

$$p_{n_x,j,k} = q_{0,j,k}, \quad 0 \le j \le n_y, \quad 0 \le k \le n_z$$

For $C^1$ continuity, in addition to the above equation, the following is required:

$$(p_{n_x,j,k} - p_{n_x-1,j,k}) = (q_{1,j,k} - q_{0,j,k}), \quad 0 \le j \le n_y, \quad 0 \le k \le n_z$$

It is noted that due to the grid topology, internal junctions are regular (valence 8).

At 132 of FIG. 1B, an analysis is optionally performed to evaluate connectivity and/or smoothness among the connected tiles of the tile arrangement. The analysis may be performed when different tiles are used, optionally randomly created tiles in which each tile may be unique. The analysis to evaluate connectivity and/or smoothness may be performed in association with the process of arranging the tiles within the domain of the deformation map to create the tile arrangement (as described with reference to act 130).

The analysis may include computation of a single globally connected component. The single globally connected component may be computed by ensuring a topological surface connectivity between all of the tiles of the tile arrangement.

The construction of the $f^{qrs}$ trivariate results in $C^1$ implicit tiles. However, the tiles might form several disconnected components, globally, which is likely to be undesired. For example, when manufactured, such microstructure with disconnected components might be at increased risk of fracture and/or breaking, in comparison to a microstructure of a single globally connected component. To create one globally component both local (intra-cell) and global (inter-cell) connectivity may be enforced.

An exemplary method of ensuring global connectivity is now described. The topological surface connectivity may be ensured by computing a graph having vertices according to centers of each of the different tiles of the tile arrangement (i.e., within the grid of the domain of the deformation map that defines the tile arrangement). Edges of the graph are according to connections between neighboring tiles that have connecting surfaces. A first spanning tree is computed according to edges of the graph that connects the tiles. All of the tiles are connected into a single global component when the first spanning tree includes all of the tiles. The edges included in the first spanning tree are removed from the graph to, possibly, create a second graph. A second spanning tree is computed according to the second graph. A third spanning tree may be similarly computed. It is noted that, possibly, a maximum of 3 spanning trees may be computed, as when each cell has six boundary surfaces. One or more of the trees may be adjusted to improve the connection between the first tree with the second (or third) trees, when creating the single global component.

In terms of mathematical representation, a graph G is constructed, consisting of the centers of the cells as its vertices, and all (up to six) edges that connect the centers of neighboring cells that share a face. A spanning tree (e.g., as described with reference to Cormen, T. H., 2009. *Introduction to algorithms. MIT press*), denoted L1, includes edges in G that connects all the cells, is constructed. The spanning tree may be computed, for example, by selecting a seed edge in G and performing a depth first search until all the cells are visited. If possible, a second spanning tree L2, is optionally constructed in the same way after removing all the edges of L1 from G. L1 and L2 have no edge in common. A third tree, L3, can be similarly created. When each tree, L1, that passes through a cell intersects two (or more) faces of the cell (except for leaf cells in L1), and when each cell has six faces, the maximal possible number of such trees is three. The existence of L2 depends on L1, and is not necessarily possible to find L2 (nor L3). However in practice, cases for which no L2 was found are rare. There could be at most three disjoint spanning trees. Further, it is the users choice to use one, two or three trees, if exists.

The connectivity graph L=L1 {∪L2} is considered as all the edges in L1 (and L2, and possibly L3). When L2 is provided, the graph L ensures connectivity of two, indicating that every two cells are connected with two separate paths, optionally improving the stability of the resulting physically manufactured microstructure. Each edge e∈L, represents a boundary face b shared between two neighboring cells. For example, cells $C_{q,r,s}$ and $C_{q+1,r,s}$ having implicit trivariates $f_{q,r,s}$ and $f_{q+1,r,s}$ respectively, with coefficients $p_{i,j,k}$ and $q_{i,j,k}$, share boundary face b (as described herein). Since the trivariates are represented as B-spline functions with an open end condition, the values of the trivariates on boundary b depends only on the control coefficients that lie on b, namely $p_{nx,j,k}$ (=$q_{0,j,k}$). Hence, the zero set restricted to b, is the (implicit) curve connecting cells $C_{q,r,s}$ and $C_{q+1,r,s}$, and depends only on these coefficients. To make sure the zero set is not empty on face b, the coefficients $\{p_{nx,j,k}\}$ are initialized to negative values, and an iterative process that increases the number of positive coefficients from $\{p_{nx,j,k}\}$ on even iterations, and in odd iterations, the values of $\{p_{nx,j,k}\}$ are increased until the zero set is no longer empty on b. It is noted that the process of increasing the positivity of the coefficients is exemplary, and other processes may be employed. Detecting a non-empty b is accomplished by sampling b until both positive and negative samples are detected. $\{q_{0,j,k}\}$ are assigned the same values computed for $\{p_{nx,j,k}\}$.

The described exemplary process ensures that the zero set of the implicit trivariates is properly shared with its neighbors.

An exemplary process is described for controlling the internal coefficients of the trivariate in order to guarantee the zero set inside the cell is forming one connected component. By repeatedly increasing the positive valued internal coefficients (except for coefficients of first layers in each direction that ensure $C^1$) as discussed herein with reference to the iterative process, the components of the zero set inside the cell connect together into a single component. As in the limit when all internal coefficients are positive, the entire cell is inside, up to the boundary conditions. After each such iteration, the zero set is extracted and examined, and the process continues until the zero set in the cell is found to form a single connected component.

Reference is now made to FIG. 10, which is a schematic depicting an example of a first spanning tree (L1) 402 computed for tile structure 404, in accordance with some embodiments of the present invention. First spanning tree 402 provides an indication that all eight tiles in tile structure 404 are connected into a single global component. First spanning tree 402 provides an indication that all eight tiles in tile structure 404 have both intra-cell connectivity and inter-cell connectivity. Grid 406 that includes eight cells is presented for reference. It is noted that no second spanning tree exists.

Figure 17:
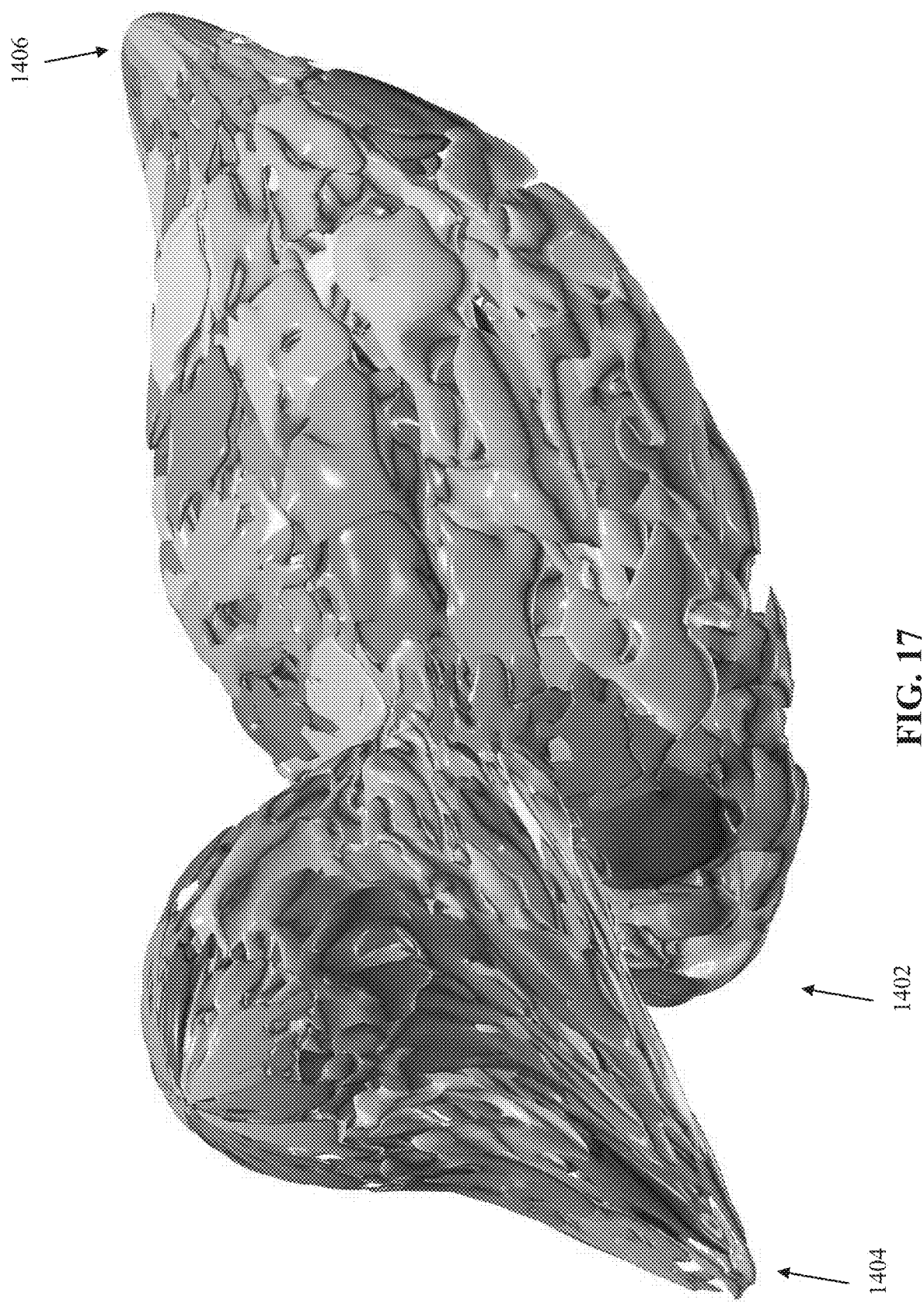
FIG. 17 is a schematic of a micro-structure of random tiles composed into a duck trivariate, in accordance with some embodiments of the present invention.

Reference is also made to FIG. 6, which is a schematic including a connectivity graph 502, that includes two spanning trees, used to ensure a single globally connected component of the tile arrangement for construction of a microstructure of a duck 1402 from random tiles shown in FIG. 17, in accordance with some embodiments of the present invention.

At 134 of FIG. 1B, the tile arrangement may be sealed along boundary surfaces of the trivariate deformation map. The sealing of the tile arrangement is designed to create a water tight boundary representation of the microstructure. The microstructure is designed to be water tight when manufacture by the manufacturing device according to the representation.

Optionally, the tile arrangement is sealed by capping open holes of the tile arrangement along boundary surfaces of the trivariate deformation map. The capping surfaces are integrated into the tile arrangement and are composed with the tile arrangement according to the deformation map.

Alternatively or additionally, the tile arrangement is sealed by computing a shell having a predefined thickness that encompasses the tile arrangement along boundary surfaces of the trivariate deformation map. The thickness may be set, for example, manually by a user via the GUI presented on the display of the client terminal, automatically computed by code, and/or defined as a preset system parameter.

Figure 11:
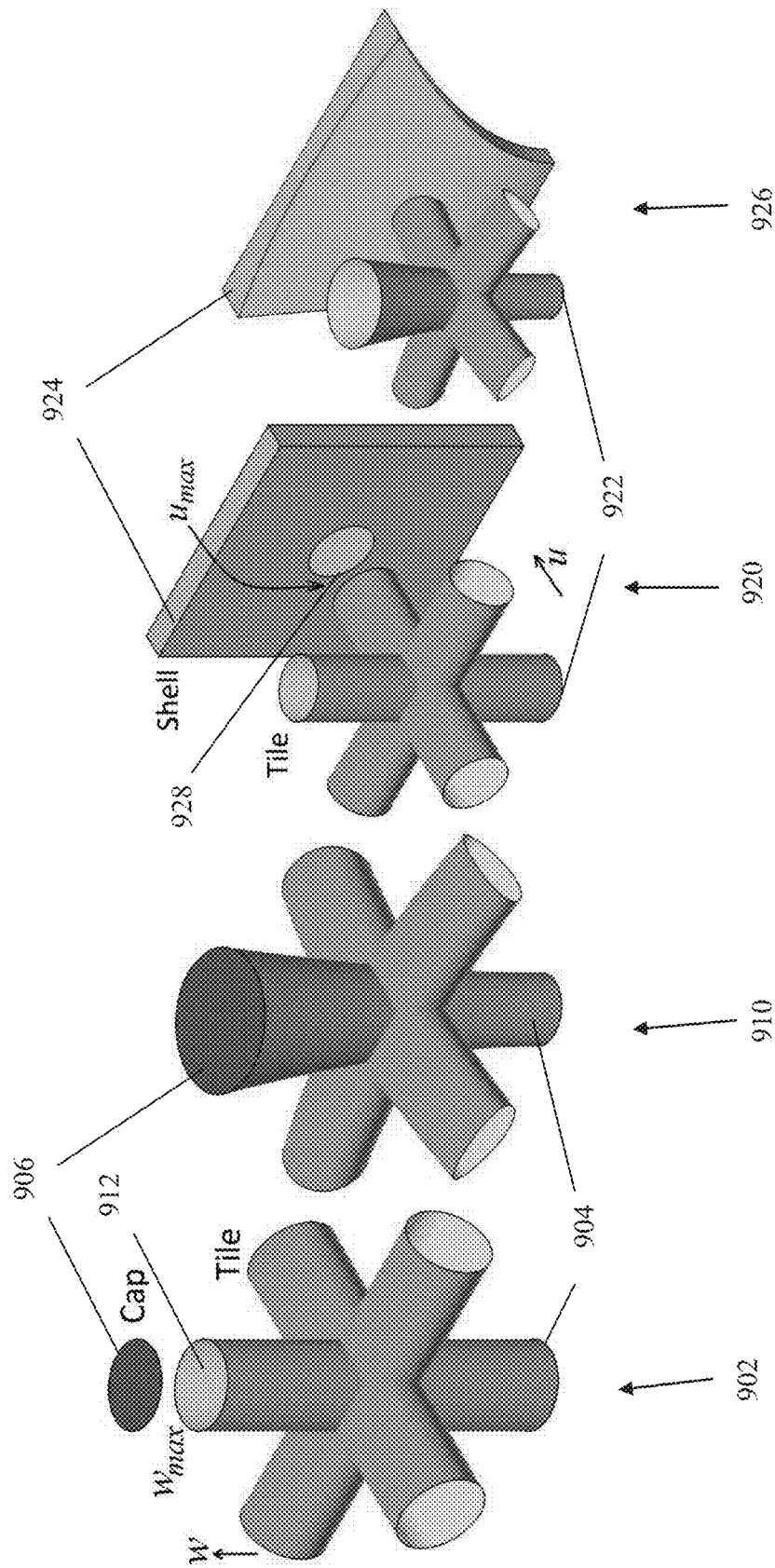
FIG. 11 includes schematics depicting capping of a hole of a tile, and shelling of a hole of another tile, in accordance with some embodiments of the present invention.

Reference is now made to FIG. 11, which includes schematics depicting capping of a hole of a tile, and shelling of a hole of another tile, in accordance with some embodiments of the present invention. Schematic 902 depicts a tile 904 with a hole 912 and a computed cap 906 (which is not yet connected to the tile). Tile 904 includes three open cylindrical surfaces. The capping is performed along the $w=w_{max}$ surface. Another schematic 910 depicts cap 906 covering hole 912 in the tile 904 after composition by the deformation map. Schematic 920 depicts a tile 922 with a hole 928 and shell 924 (which is not yet connected to the tile). Tile 922 includes three open cylindrical surfaces. Another schematic 926 depicts shell 924 covering hole 928 of tile 922 after composition by the deformation map.

An exemplary method of capping open holes of the tile arrangement is now discussed. For simplicity and clarity of explanation, it is assumed that the axis-aligned bounding box of the tile is the unit cube. Boundary curves are detected and extracted from the tile, when on one of the six planes of $x=0$; $x=1$; $y=0$; $y=1$; $z=0$; $z=1$, as a preprocessing step. When a copy of the tile is placed along the $u=u_{min}$ surface of the domain of D, then the boundary curves of the tile for $x=0$, if any, are used to create a planar trimmed surface which serves as a cap over the tile along that $u=u_{min}$ surface. A similar process may be used for tiles placed along all boundaries of D.

For implicit tiling, capping may be performed by assigning negative values to all coefficients of a face(s) that lies on the boundaries of D. The distance of the zero set from the boundary of D may be controlled by the value of the control points on the boundary.

Lemma 1: Consider a scalar Bézier curve $C(t)=\Sigma_{i=0}^n p_i \theta_{i,m}(t)$ and assume $|p_i| \leq 1$ for $1 \leq i \leq n$. If $C(t_0)=0$, for some $t_0$, then it holds that $$t_0 \geq 1 - \sqrt[n]{\frac{1}{1-p_0}}.$$

Proof:

Because $0 = C(t_0) = \sum_{i=0}^{n} p_i \theta_{i,n}(t_0)$, we have, $$p_0(1-t_0)^n = \sum_{i=1}^{n} -p_i \theta_{i,n}(t_0) \geq \sum_{i=1}^{n} -\theta_{i,n}(t_0) = (1-t_0)^n - 1.$$

In other words, $$(1-p_0)(1-t_0)^n \leq 1 \text{ and } t_0 \geq 1 - \sqrt[n]{\frac{1}{1-p_0}}.$$

Similar behavior to Lemma 1 may be expected from B-spline curves with open end conditions. Considering the coefficients of trivariates $f^{qrs}$ of a cell that is on the boundary of D. The order of the summations in the above equation may be arranged such that the inner most summation is orthogonal to the boundary. Assume without loss of generality that this direction is the z direction. Then:

$$f^{qrs}(x,y,z) = \sum_{i=0}^{n_x}\sum_{j=0}^{n_y}\sum_{k=0}^{n_z} p_{i,j,k} B_{i,d_x}(x) B_{j,d_y}(y) B_{k,d_z}(z)$$

$$= \sum_{i=0}^{n_x}\sum_{j=0}^{n_y} c_{ij}(z) B_{i,d_x}(x) B_{j,d_y}(y), \text{ where,}$$

$$c_{ij}(z) = \sum_{k=0}^{n_z} p_{i,j,k} B_{k,d_z}(z).$$

Therefore, based on Lemma 1 and representing $f^{qrs}$ as $(n_x+1)(n_y+1)$ curves, the distance between the zero set of $f^{qrs}$ (x,y,z) and the boundary of D may be set (e.g., by a user via the GUI, and/or automatically by code). Lemma 1 provides a lower bound of the distance (ranging from 0 to 1) of the zero set from the boundary. If $p_{i,j,0}=0$ the zero set is on the boundary (assuming $p_{i,j,0} \neq 0$, $\forall k>1$), and as $p_{i,j,0}$ gets smaller (having a negative value), the zero set moves inside.

An exemplary method of computing a shell is now described. A preprocessing step for extracting the boundary curves of the tile may be performed, as described above with reference to the exemplary method for computing the cap. Two planar surfaces may be created, representing the outer and inner shells, which have opposite orientations. The inner surface is trimmed using the appropriate boundary curves of the tile, but with reversed orientation. The outer and the inner surfaces are joined using four planar surfaces to form a closed (trimmed) box. For the case of implicit tiling, the shelling may be created by assigning positive values to all coefficients of faces on the boundary of D, and adding the original boundary surfaces of D.

At 140, the representation of the microstructure is created, as described with reference to act 140 of FIG. 1A.

At 142, the degree of the representation of the microstructure may be optionally reduced, by reducing the degrees of all freeform(s) representing the tiles. The degree reduction of the representation of the microstructure can maintains smoothness and/or continuity between tiles.

Reduction of the degree of the representation of the microstructure improves computational efficiency of the computing device that computes the representation of the microstructure. The functional composition operation of parametric forms described herein may result in geometries with high degrees. In addition to the large space complexity, higher computational costs may be incurred, for example, in terms of processor utilization and/or data storage requirements. A lower degree approximation of microstructures may be performed by using quadratics and/or cubics, while preserving continuity between glued patches.

Optionally, the degree of the representation of the microstructure is reduced by approximating freeform(s) of the representation of the microstructures as quadratic degrees and/or cubic degrees. End/corner points of approximated freeform(s) are interpolated. Tangents at end/corner points of cubic degree(s) approximated freeform(s) are reconstructed. The interpolation of the end/corner point of the freeform(s) and/or reconstruction of the tangents ensures connectivity and sometimes of the tiles.

The degree reduction based on approximation may be performed according to the following exemplary process: B-spline entities in the constructed microstructure representation are divided into Bézier entities. Bézier curves in the composed tiles are approximated by quadratic and/or cubic Bézier curves using an approximation that ensure interpolation of the end points and/or reconstruction of tangents at the end points (i.e., in the cubic case). Bézier surfaces are reconstructed from four boundary Bézier curves, optionally based on the interior surface control point(s) to reduce approximation error, for example, in a least squares sense. Bézier trivariates are reconstructed from six boundary Bézier surfaces, optionally based on the interior trivariate control point(s) to reduce approximation error, for example, in least squares sense.

In an example, two adjacent high order freeforms share a common face F of a lower dimension. Both freeforms are approximated using the same approximation process described herein. The boundary of an approximated (e.g., Bézier) freeform, denoted A(F), is only affected by the input shared boundary, F. Hence, both approximated freeforms share a common face A(F), ensuring continuity.

Figure 12:
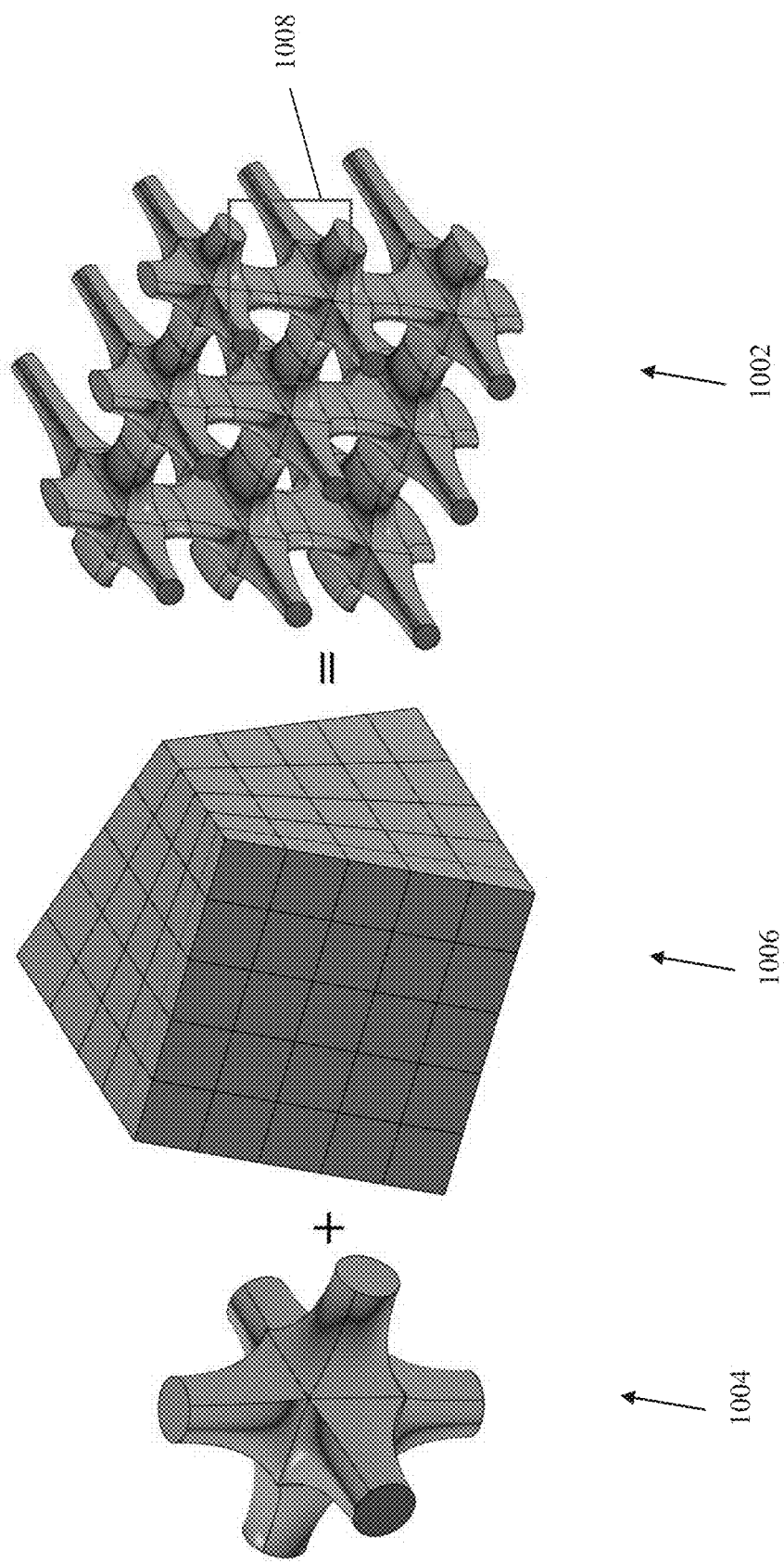
FIG. 12 is a schematic of a representation of a microstructure prior to degree reduction, in accordance with some embodiments of the present invention.

Reference is now made to FIG. 12, which is a schematic of a representation of a microstructure 1002 prior to degree reduction, in accordance with some embodiments of the present invention. Microstructure 1002 is created based on a tile 1004 that includes seven trivariates, which is arranged and composed into a deformation map 1006. The degrees of tile 1004, deformation map 1006, and microstructure representation 1002 in (u, v, w) are respectively (3, 3, 2), (1, 1, 2) and (12, 12, 8). The region of microstructure representation 1002 located within a rectangle 1008 is shown magnified in FIG. 13.

Figure 13:
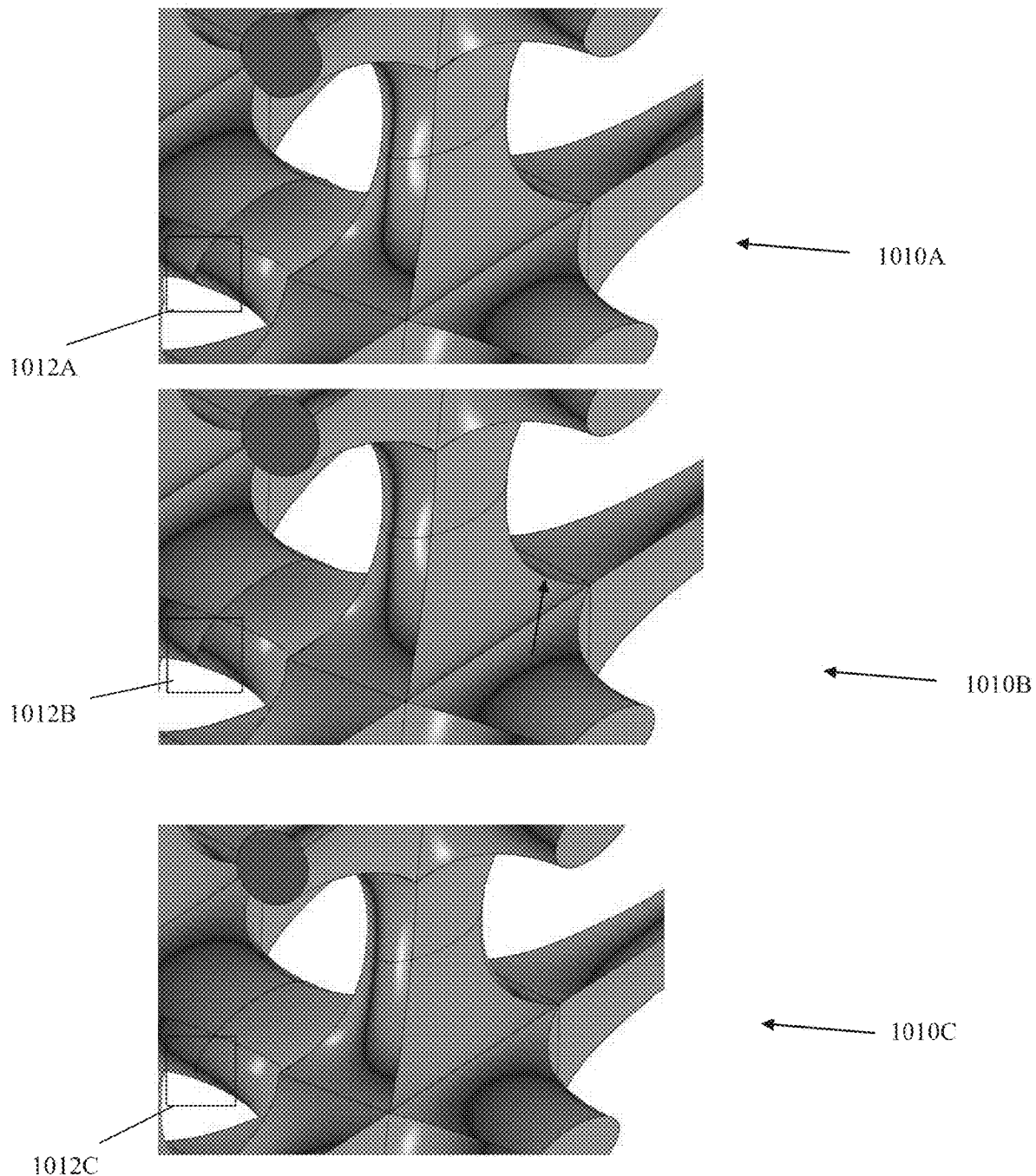
FIG. 13 is a schematic of a magnified region of a microstructure representations prior to degree reduction, and magnified regions of a microstructure representation created by reducing the degree of the microstructure representation, in accordance with some embodiments of the present invention

Reference is now made to FIG. 13, which is a schematic of a magnified region of a microstructure representations prior to degree reduction 1010A, and magnified regions of a microstructure representation 1010B-C created by reducing the degree of microstructure representation 1010A, in accordance with some embodiments of the present invention. Microstructure representation 1010A is an enlargement of the region of microstructure representation 1002 located within rectangle 1008 shown in FIG. 12. Microstructure representation 1010A is depicted prior to degree reduction, having degrees 12, 12, and 8 in the u, v, and w direction, respectively. Microstructure representation 1010B is created by performing an approximation of microstructure representation 1010A using tri-quadratics.

Microstructure representation 1010C is created by performing an approximation of microstructure representation 1010A using tri-cubics. G1 discontinuities in the surface are visible at the junction of two adjacent tiles, as depicted within blocks 1012B-C of respective microstructure representation 1010B-C. However, in practice, the G1 discontinuities are not significant, visually and/or in the manufactured physical version of the approximated microstructure representations, in comparison to corresponding junction of two adjacent tiles in block 1012A of non-approximated microstructure representation 1010A. The reason can be found in the fact that the provided tiles are usually of a low order (and hence with little information), and/or the fact that the deformation map is locally smooth.

At 150, the representation of the microstructure is stored, as described with reference to act 150 of FIG. 1A.

At 160, instructions for manufacturing the microstructure are generated, as described with reference to act 160 of FIG. 1A.

At 170, a physical version of the microstructure is manufactured according to the instructions, as described with reference to act 170 of FIG. 1A.

Various implementations of at least some of the systems and/or methods and/or code instructions stored in a data storage device executed by one or more processors delineated hereinabove and as claimed in the claims section below find experimental support in the following examples.

EXAMPLES

Reference is now made to the following examples, which together with the above descriptions illustrate some implementations of the systems and/or methods and/or code instructions stored in a data storage device executed by one or more processors described herein in a non-limiting fashion.

Inventors implemented the systems and/or methods and/or code instructions described herein using the IRIT solid modeling kernel, for example, as described with reference to Elber, G., January 2017. *Irit modeling environment*. "http://www(dot)cs(dot)technion(dot)ac(dot)il/_irit/". The examples were computed on a 3.4 GHz Intel i7 CPU with 32 GB RAM in a single thread mode and Windows 7 and took less than 5 seconds to generate. The memory footprints were less than 400 MB.

Figure 14:
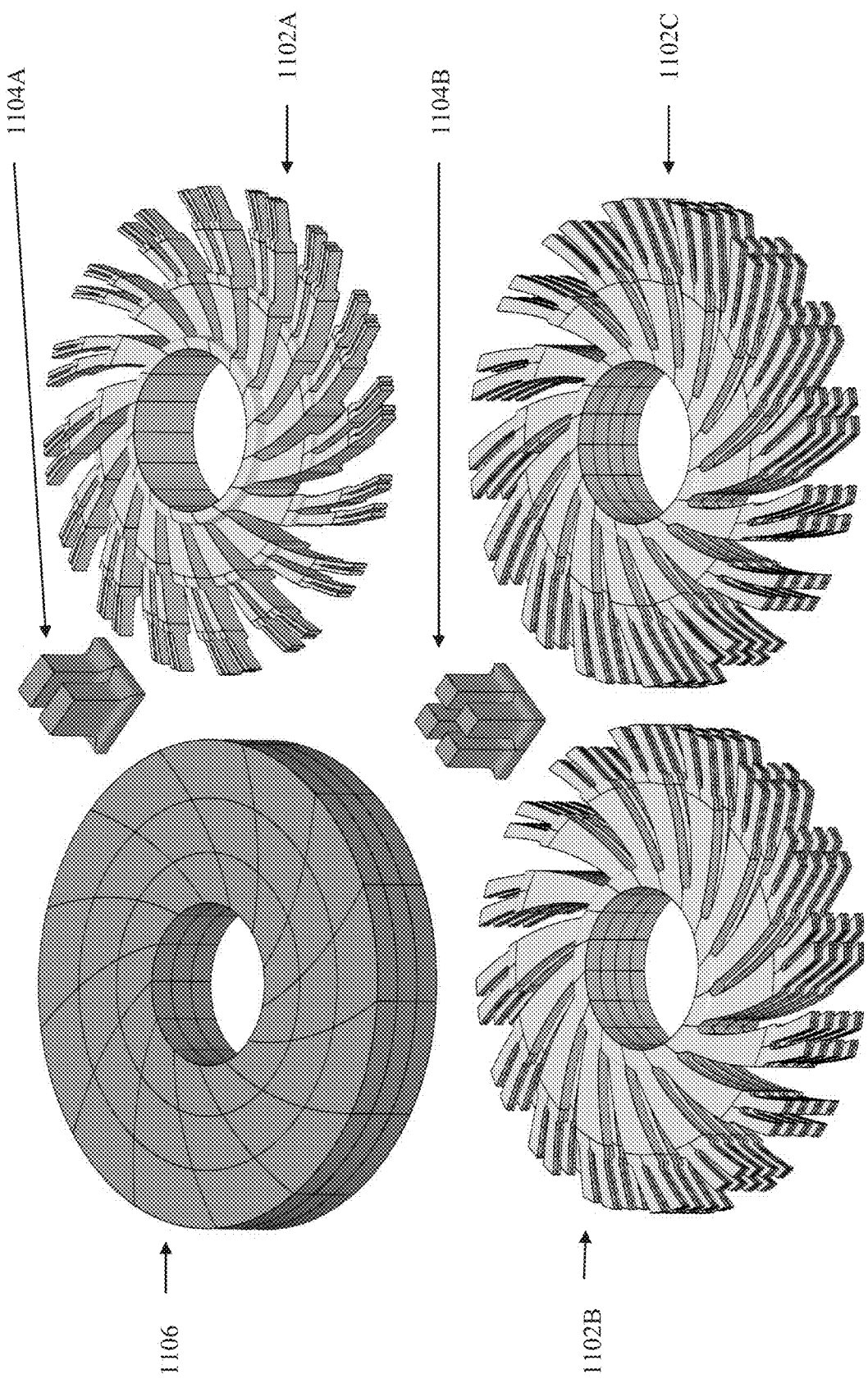
FIG. 14 is a schematic depicting computation of a representation of circular heat-sinks, based on a heat-sink design for LEDs, in accordance with some embodiments of the present invention.

Reference is now made to FIG. 14, which is a schematic depicting computation of a representation of circular heat-sinks 1102A-B, based on a heat-sink design for LEDs, for example, as described with reference to Bornoff et al., and RapidLED, 2017. *Single LED heat sinks*. "https://www(dot)rapidled(dot)com/single-led-heat-sink/", in accordance with some embodiments of the present invention. Trivariate tiles 1104A-B have (1,0) and (1,1) discontinuities respectively, along the (u, v) directions. Tile 1104A has one discontinuity along the u direction. The degrees of tile 1104A, deformation map 1106, and created representation of microstructure 1102A in (u, v, w) are (2, 2, 3), (3, 1, 2) and (12, 12, 18) respectively. Tile 1104A is composed into the circular twisted deformation map 1106, with repetition counts of (16, 1) along (u, v) directions and three levels of hierarchy along the w direction, creating heat-sink 1102A. Two similar constructions 1102B-C are created using tile 1104B with two levels of hierarchy. Two different values for scaling parameters (0.5 and 0.8) along the w direction are used. Each scaling parameter reduces the size of the next higher level.

Figure 15:
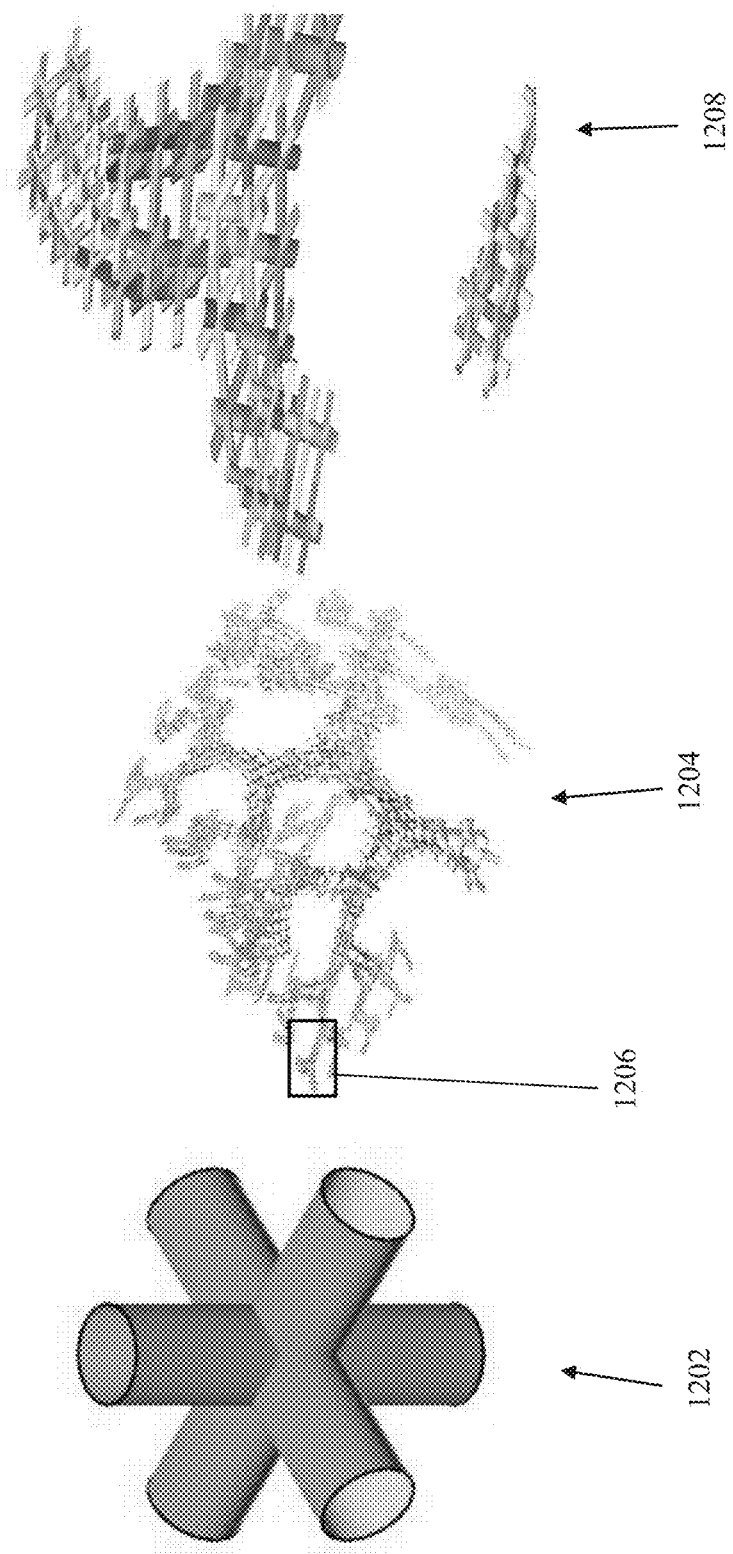
FIG. 15 is a schematic that demonstrates a sequence of two composition operations, applied one after another, creating two levels of (multi-resolution) microstructures, in accordance with some embodiments of the present invention.

Reference is now made to FIG. 15, which includes schematics that demonstrate a sequence of two composition operations, applied one after another, creating two levels of (multi-resolution) microstructures, in accordance with some embodiments of the present invention. The trivariate elements of the hierarchical micro-structure, as described with reference to FIG. 4, with tri-quadratic approximation, are used as deformation maps. The second level of microstructures arranges a bivariate tile 1202 (2, 2, 2) times in each trivariate along (u, v, w), for composing into a microstructure 1204. Capping is applied to all boundaries. The degrees of the surfaces in (u, v), in the original tile and in the final microstructure, are (3, 1) and (18, 6), respectively. Region 1206 defined by a rectangle on microstructure 1204 is shown as a magnification 1208.

Figure 16:
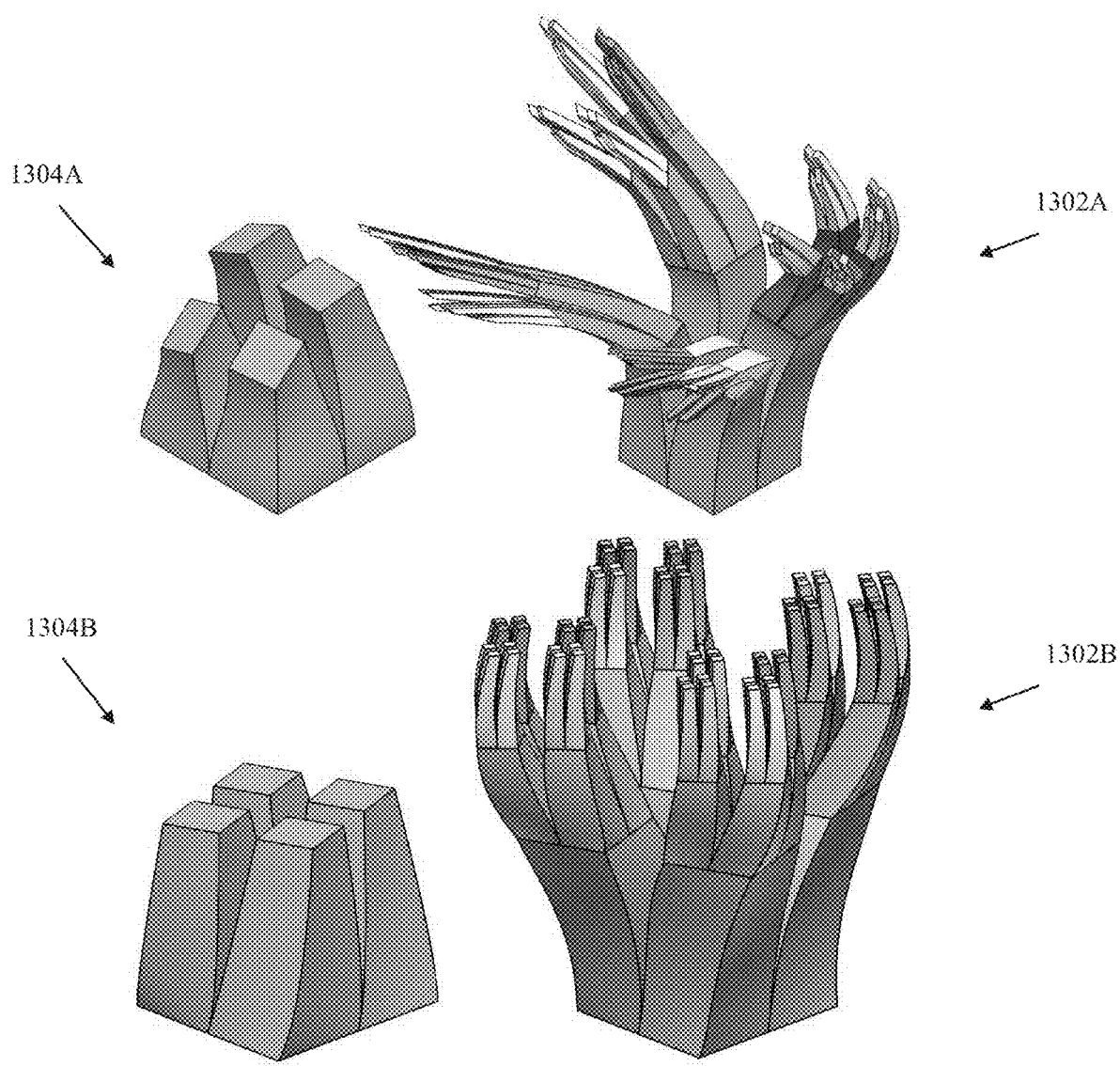
FIG. 16 is a schematic of variants of microstructures created with respective tiles with discontinuities, in accordance with some embodiments of the present invention.

Reference is now made to FIG. 16, which includes schematics of variants of microstructures 1302A-B created with respective tiles 1304A-B with discontinuities, in accordance with some embodiments of the present invention. Tiles 1304A-B include one discontinuity along u and v. Tiles 1304A-B are arranged with repetition counts of (1, 1, 3) and composed into a deformation map to obtain the hierarchical microstructures structures 1302A-B.

Reference is now made to FIG. 17, which is a schematic of a micro-structures 1402 of (4, 4, 12) random tiles composed into a duck trivariate, in accordance with some embodiments of the present invention. A tri-cubic trivariate B-spline with eight control coefficients at each direction is used for each implicit tile. A connectivity of two is ensured based on a computed connectivity graph. C1 continuity is ensured between the tiles. Micro-structure 1402 with guaranteed connectivity took 108 seconds to construct with a memory usage 293 MB.

Figure 18:
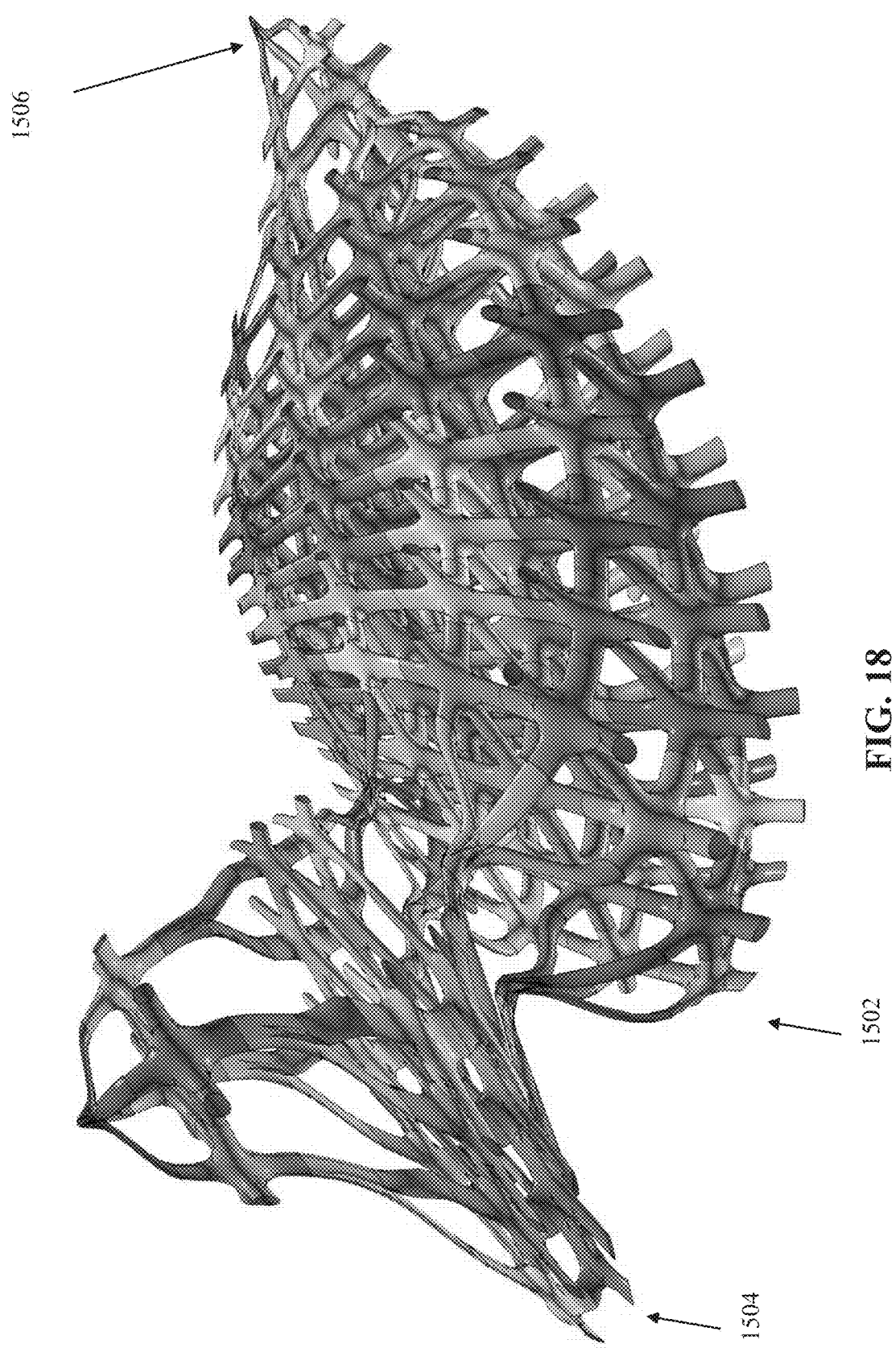
FIG. 18 is a schematic of a microstructure depicting approximate uniform tiling in object (e.g., Euclidean) space, in accordance with some embodiments of the present invention.

Reference is now made to FIG. 18, which is a schematic of a microstructure 1502 depicting approximate uniform tiling in object (e.g., Euclidean) space, in accordance with some embodiments of the present invention. Microstructure 1502 is created based on bifurcation tiles with parameteric surfaces described with reference to FIG. 9. The value of $\varepsilon=0.35$, and the length of duck 1502 is a little over 2. It is noted that the singular areas of the tip of the head 1504 and the tail 1506 of duck 1502 include a single, relatively large, 1 to 4 tile each, covering regions 1504 and 1506 of duck 1502. Contrast the size of the tiles of head 1504 and tail 1506 of duck 1502 with the size of the tiles near a head 1404 and a tail 1406 of duck 1402 of FIG. 17, which become very small.

Figure 19:
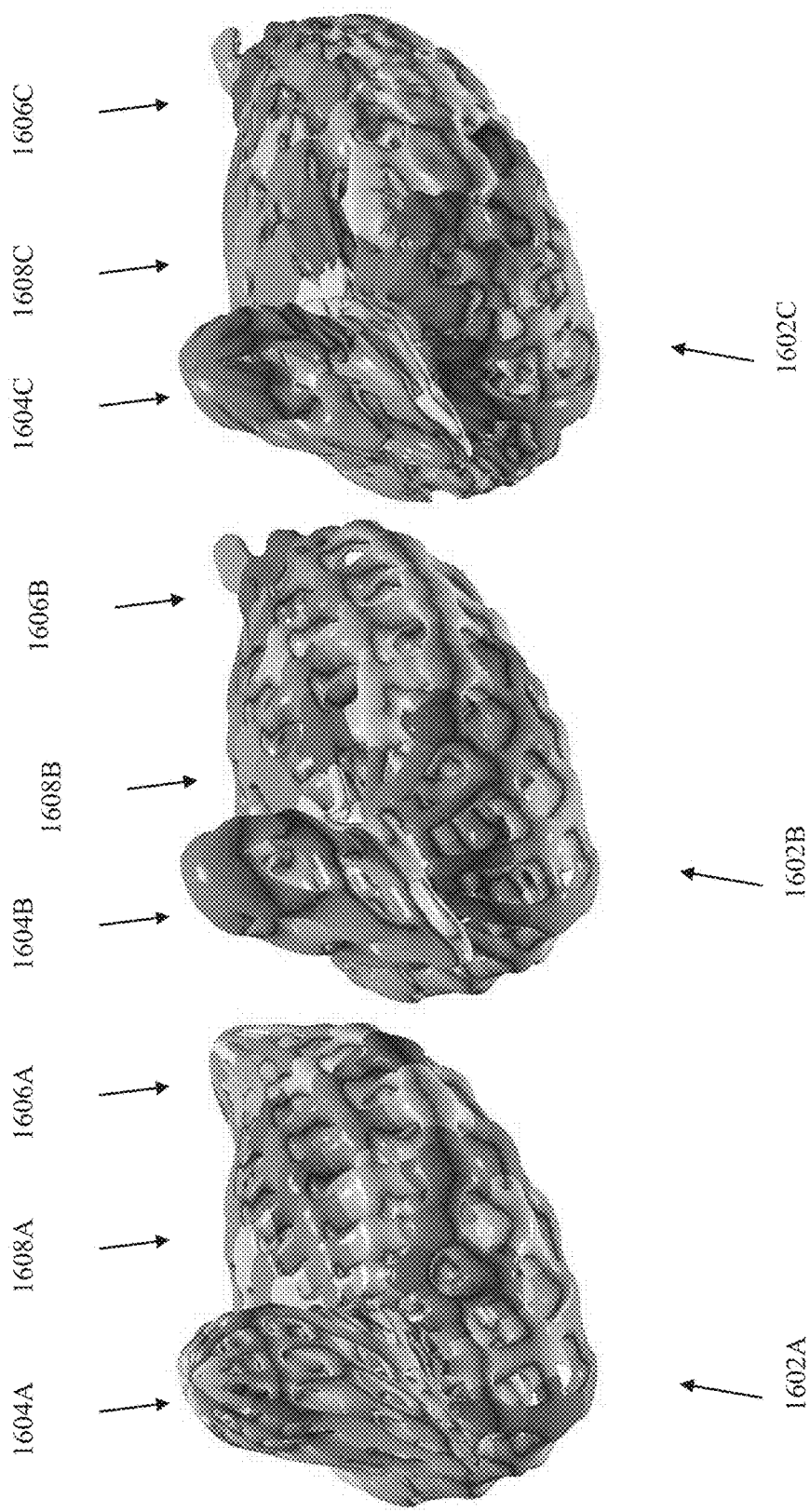
FIG. 19 is a schematic including three examples of implicit microstructures composed in a duck trivariate, in accordance with some embodiments of the present invention.

Reference is now made to FIG. 19 which is a schematic including three examples of implicit microstructures 1602A-C composed in a duck trivariate, in accordance with some embodiments of the present invention. Duck microstructure 1602A is created from an implicit tile of a 3D cross that is uniformly tiled in the parameteric space of the duck. Duck microstructure s1602B is crated using implicit bifurcation structures (with $\varepsilon=0.35$, according to the method described with reference to FIG. 5), approximating a uniform tiling in object (e.g., Euclidean) space. Duck microstructure 1602C is created using randomized tiles, setting $\alpha=0.65$ and using the mathematical relationship $p_{i,j,k}=(1-\alpha)p_{i,j,k}^o+\alpha \text{Random}(-1,1)$. It is noted that the bifurcation of the domain of the deformation map to include bifurcation cells produces substantially uniform sized tiles in the object (e.g., Euclidean) space when the representation of the structure is created. The size of the tiles of the heads 1604B-C and tails 1606B-C of ducks 1602B-1602C are substantially uniform in comparison to the tiles of the bodies 1608B-C of ducks 1602B-1602C, in contrast to the size of the tiles of the head 1604A and tail 1606A of duck 1602A which are much smaller in comparison to the tiles of the body 1608A of duck 1602A.

The duck model with bifurcation tilings shown in FIG. 6 and FIG. 19 took less than 4 seconds each to generate with a memory usage of 104 MB.

Figure 20:
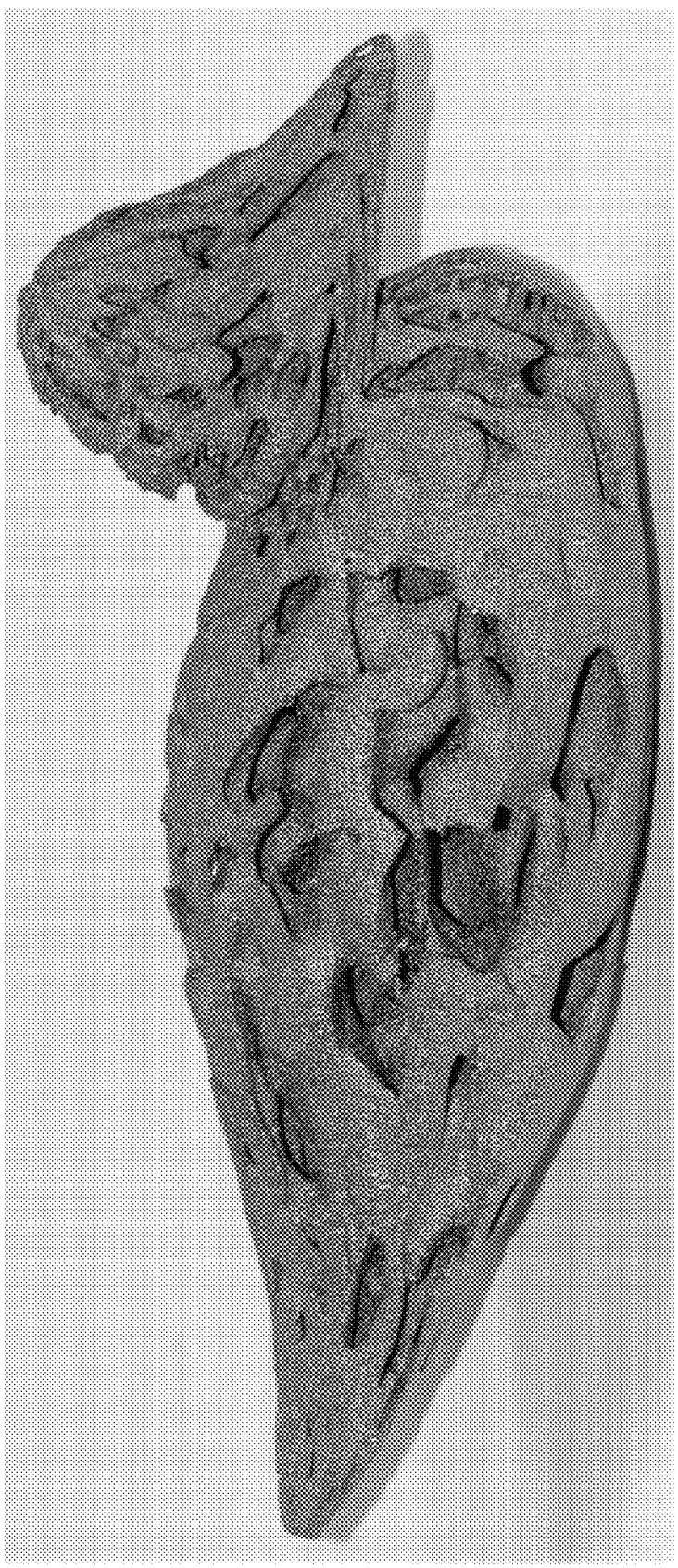
FIG. 20 is an image of a physical replica of a microstructure created from random tiles arranged as a duck printed from titanium, in accordance with some embodiments of the present invention.

Reference is now made to FIG. 20, which is an image of a physical replica 1702 of a micro-structure created from random tiles composed in a duck trivariate that is 3D printed from titanium, demonstrating the watertightness of the physical duck, in accordance with some embodiments of the present invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant additive manufacturing devices will be developed and the scope of the term additive manufacturing device is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of generating instructions for manufacturing a microstructure by a manufacturing device, comprising:
    providing a representation of a freeform tile,
    wherein said freeform tile is represented as a polynomial or rational spline denoted T;
    providing a representation of a deformation map that maps a parameter space to a space of an object,
    wherein said deformation map is represented as a polynomial or rational spline denoted M;
    arranging a plurality of instances of the freeform tile within at least a portion of a domain of the deformation map to create a tile arrangement;
    creating a representation a microstructure of the object denoted M' by mathematically functionally composing the tile arrangement into the deformation map denoted M'=M(T); and
    providing code instructions for execution by a manufacturing device controller of a manufacturing device for manufacturing the microstructure.

2. The method of claim 1, further comprising: reducing the degree of the representation of the microstructure by approximating freeforms of the representation of the microstructures as lower order degrees.

3. The method of claim 2, wherein each of the tiles of the tile arrangement is randomly generated, wherein each of the randomly generated tiles is created within a respective cell of a grid of the domain of the deformation map, wherein the tiles are randomly generated according to similar control coefficients along common boundaries of respective cells of the grid to create continuity between adjacent randomly generated tiles.

4. The method of claim 1, further comprising providing a plurality of different freeform(s) tiles, wherein the tile arrangement is created by arranging the plurality of different tiles within the domain of the deformation map, and further comprising computing a single globally connected component of the tile arrangement by ensuring a topological connectivity between all of the tiles of the tile arrangement.

5. The method of claim 4, wherein the topological connectivity is ensured by:
    computing a graph having vertices according to centers of each tile of the tile arrangement, and edges of the graph are according to connections between neighboring tiles that have connecting faces;
    computing a first spanning tree according to edges of the graph that connects the tiles of the tile arrangement,
    wherein all of the tiles of the tile arrangements are connected into a single global component when the first spanning tree includes all of the tiles of the tile arrangement.

6. The method of claim 5, further comprising:
    removing the edges included in the first spanning tree from the graph to create a second graph;
    computing a second spanning tree according to the second graph; and
    adjusting at least one of the tiles of the tile arrangement to connect the first graph and the second graph for creating the single global component.

7. The method of claim 1, further comprising: creating a non-grid topology by subdividing the domain of the deformation map into a plurality of cells, wherein each of the tiles of the tile arrangement located in a respective cell of the plurality of cells is mapped by a respective subdivision of the domain of the deformation map to a same size in object space within a tolerance requirement.

8. The method of claim 7, wherein at least one of the tiles of the tile arrangement includes an automatically created bifurcated tile computed according to bifurcation cells created by the subdivision of the domain of the deformation map.

9. The method of claim 7, wherein domain of the deformation map is divided to include bifurcation cells according to bifurcation tiles of the tile arrangement.

10. The method of claim 1, further comprising sealing the tile arrangement along the boundaries of the deformation map.

11. The method of claim 10, wherein sealing comprises capping open holes of the tile arrangement of the tile along boundaries of the deformation map.

12. The method of claim 10, wherein sealing comprises creating a shell having a predefined thickness that encompasses the tile arrangement along boundaries of the deformation map.

13. The method of claim 1, wherein at least one surface of each of the plurality of instances of the freeform tile coincides and is connected with at least one other surface of another of at least one of the plurality of instances of the freeform tile creating smooth continuity between the tiles of the tile arrangement.

14. The method of claim 1, wherein a single branch-in surface and one or more branch-out surfaces are defined for the tile, wherein the tile arrangement is created by iteratively mapping the respective single branch-in surface of each of the tiles at a next level to a respective branch-out surface of each tile at a current level.

15. The method of claim 14, wherein the single branch-in surface is larger than each of the one or more branch-out surfaces, wherein a volume of each of the tiles of the tile arrangement at the next level is adjusted such that the respective single branch-in surface of each of the tiles at the next level is continuous with the respective branch-out surface of each tile at the current level.

16. The method of claim 14, wherein the iterations for arranging the tiles are performed for a predefined number of tile levels for filing at least the portion of the domain of the deformation map.

17. The method of claim 14, wherein the one or more branch-out surfaces are based on a geometric bifurcation of the tile created by a partial Euclidean discontinuity.

18. The method of claim 14, wherein the single branch-in surface and each of the one or more branch-out surfaces are designated according to a plurality of boundary surfaces of the tile.

19. The method of claim 1, wherein the deformation map and the tile are implemented from the group consisting of: non-trimmed Bezier parametric splines, non-trimmed B-spline parametric splines, trimmed Bezier parametric splines, and trimmed B-spline parametric splines.

20. A system for generating instructions for manufacturing a microstructure by a manufacturing device, comprising:
at least one hardware processor executing a code for:
receiving a representation of a freeform tile,
wherein said freeform tile is represented as a polynomial or rational spline denoted T;
receiving a representation of a deformation map that maps a parameter space to a space of an object,
wherein said deformation map is represented as a polynomial or rational spline denoted M;
arranging a plurality of instances of the freeform tile within at least a portion of a domain of the deformation map to create a tile arrangement;
creating a representation a microstructure of the object denoted M' by mathematically functionally composing the tile arrangement into the deformation map denoted M'=M(T); and
outputting code instructions for execution by a manufacturing device controller of a manufacturing device for manufacturing the microstructure.

* * * * *